United States Patent
Chen et al.

(10) Patent No.: US 12,018,661 B2
(45) Date of Patent: Jun. 25, 2024

(54) HUMIDITY-RESPONSIVE TRIPEPTIDE CRYSTAL

(71) Applicant: Research Foundation of the City University of New York, New York, NY (US)

(72) Inventors: Xi Chen, New York, NY (US); Rein Ulijn, New York, NY (US); Roxana Piotrowska, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 628 days.

(21) Appl. No.: 17/140,639

(22) Filed: Jan. 4, 2021

(65) Prior Publication Data

US 2021/0404450 A1 Dec. 30, 2021

Related U.S. Application Data

(60) Provisional application No. 63/132,706, filed on Dec. 31, 2020, provisional application No. 62/956,470, filed on Jan. 2, 2020.

(51) Int. Cl.
| | |
|---|---|
| *F03G 7/06* | (2006.01) |
| *C07K 5/087* | (2006.01) |
| *C07K 5/093* | (2006.01) |
| *C07K 5/097* | (2006.01) |
| *C08L 7/00* | (2006.01) |
| *C08L 21/02* | (2006.01) |
| *C08L 67/02* | (2006.01) |
| *C08L 69/00* | (2006.01) |
| *C08L 79/08* | (2006.01) |
| *C08L 83/04* | (2006.01) |

(52) U.S. Cl.
CPC ............. *F03G 7/06* (2013.01); *C07K 5/0812* (2013.01); *C07K 5/0819* (2013.01); *C07K 5/0821* (2013.01); *C08L 7/00* (2013.01); *C08L 21/02* (2013.01); *C08L 67/02* (2013.01); *C08L 69/00* (2013.01); *C08L 79/08* (2013.01); *C08L 83/04* (2013.01); *C08L 2203/16* (2013.01)

(58) Field of Classification Search
CPC . F03G 7/06; C08L 79/08; C08L 67/02; C08L 83/04; C08L 69/00; C08L 2203/16; C08L 21/02; C08L 7/00; C07K 5/0821; C07K 5/0812
See application file for complete search history.

(56) References Cited

U.S. PATENT DOCUMENTS

2019/0309735 A1  10/2019  Chen

FOREIGN PATENT DOCUMENTS

| WO | WO2010103326 | 9/2010 |
|---|---|---|
| WO | WO2012071426 | 5/2012 |
| WO | WO2015172067 | 11/2015 |

OTHER PUBLICATIONS

Arazoe et al., An autonomous actuator driven by fluctuations in ambient humidity, Nature Materials, vol. 15, Oct. 2016 (Year: 2016).*
Chin et al., Covalent-supramolecular hybrid polymers as muscle-inspired anisotropic actuators, Nature Communications vol. 9, p. 2395 (2018). (Year: 2018).*
Chen, X. et al. Scaling up nanoscale water-driven energy conversion into evaporation-driven engines and generators. Nat. Commun. 6, 7346, (2015).
Chen, X., Mahadevan, L., Driks, A. & Sahin, O. Bacillus spores as building blocks for stimuli-responsive materials and nanogenerators. Nat. Nanotechnol. 9, 137-141, (2014).
Ma, M., Guo, L., Anderson, D. G. & Langer, R. Bio-inspired polymer composite actuator and generator driven by water gradients. Science 339, 186-189, (2013).
Arazoe, H. et al. An autonomous actuator driven by fluctuations in ambient humidity. Nat. Mater. 15, 1084-1089, (2016).
Shin, B. et al. Hygrobot: A self-locomotive ratcheted actuator powered by environmental humidity. Science Robotics 3, 2629 (2018).
Chin, S.M., Synatschke, C.V., Liu, S. et al. Covalent-supramolecular hybrid polymers as muscle-inspired anisotropic actuators. Nat Commun 9, 2395 (2018).
Kim, S. H. et al. Bio-inspired, Moisture-Powered Hybrid Carbon Nanotube Yarn Muscles. Sci. Rep. 6, 23016, (2016).
Chen, P. N. et al. Hierarchically arranged helical fibre actuators driven by solvents and vapours. Nat. Nanotechnol. 10, 1077 (2015).
Carter, N. A. & Grove, T. Z. Protein Self-Assemblies That Can Generate, Hold, and Discharge Electric Potential in Response to Changes in Relative Humidity. J. Am. Chem. Soc. 140, 7144-7151, (2018).
Zhang, L., Bailey, J. B., Subramanian, R. H., Groisman, A. & Tezcan, F. A. Hyperexpandable, self-healing macromolecular crystals with integrated polymer networks. Nature 557, 86-91, (2018).
Katsoulidis, A. P. et al. Chemical control of structure and guest uptake by a conformationally mobile porous material. Nature 565, 213-217 (2019).
Dai, M. et al. Humidity—Responsive Bilayer Actuators Based on a Liquid-Crystalline Polymer Network. ACS Appl. Mater. Interfaces 2013, 5, 11, 4945-4950 (2013).
Piotrowska, R., Hesketh, T., Wang, H. et al. Mechanistic insights of evaporation-induced actuation in supramolecular crystals. Nat. Mater. 20, 403-409 (2021).

\* cited by examiner

*Primary Examiner* — Robert D Harlan
(74) *Attorney, Agent, or Firm* — Peter J. Mikesell; Schmeiser, Olsen & Watts, LLP

(57) ABSTRACT

A thin film that has a flexible polymer layer and a peptide layer. The peptide layer is disposed on the flexible polymer layer and has a peptide selected from HYF, DYF and YFD. The thin film reversibly curves with changes in humidity.

12 Claims, 23 Drawing Sheets

HYF

DYF

YFD

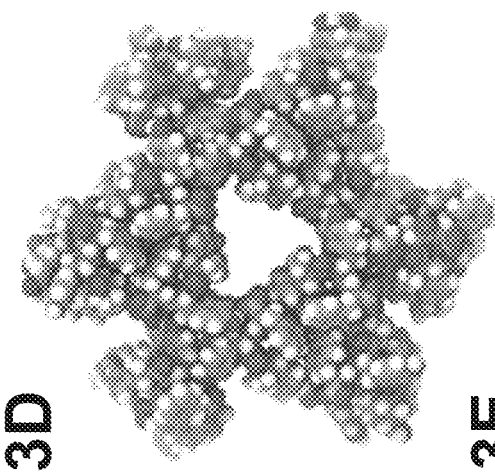
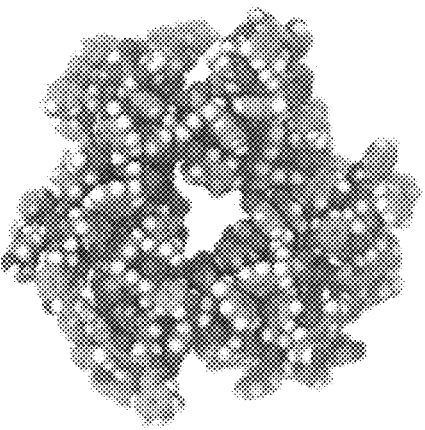
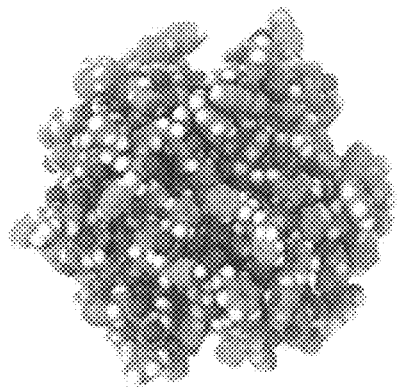
FIG. 3D  HYF
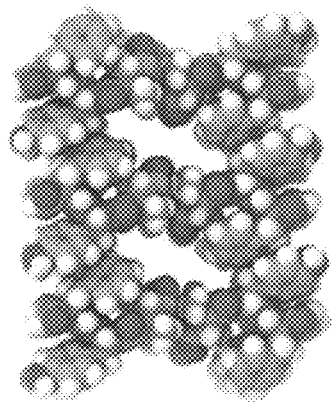
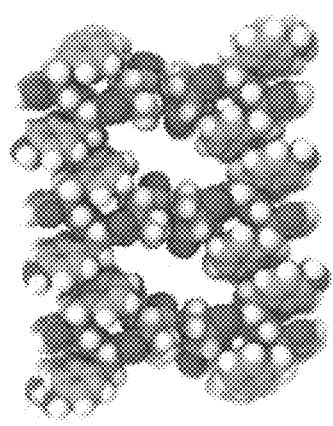
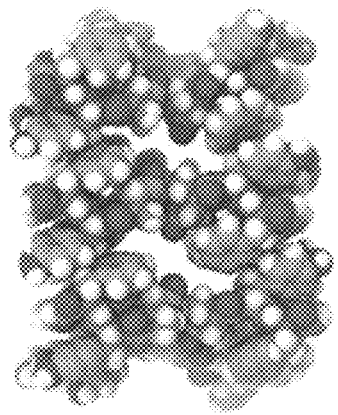
FIG. 3E  DYF

HUMIDITY-RESPONSIVE TRIPEPTIDE CRYSTAL

CROSS-REFERENCE TO RELATED APPLICATIONS

This application claims priority to and is a non-provisional of U.S. Patent Application 62/956,470 (filed Jan. 2, 2020) and U.S. Provisional Application 63/132,706 (filed Dec. 31, 2020), the entirety of which are incorporated herein by reference.

STATEMENT OF FEDERALLY SPONSORED RESEARCH OR DEVELOPMENT

This invention was made with government support under grant numbers N00014-18-1-2492 and FA9550-19-1-0111 awarded by the United States Office of Naval Research and the Air Force Office of Scientific Research, respectively. The government has certain rights in the invention.

BACKGROUND OF THE INVENTION

Water-responsive (WR) materials that exhibit dramatic structural responses to relative humidity (RH) changes open opportunities to harvest and utilize evaporation energy and can be used as high-efficiency RH-driven actuators for applications such as soft robotics and wearable devices. WR materials that have been described to date include both naturally derived and fully synthetic structures. For instance, π-stacked carbon nitride polymer demonstrates extremely fast (50 ms) WR deformation; zinc-based metal-organic frameworks (MOFs) have recently been developed for water sensing and as thermal imaging probes; and carbon nanotube and graphene-based materials show remarkably high WR energy densities.

In nature, WR behaviors are crucial for life-critical biological functions such as the opening and closing of pinecones or propelling of wheat awns into the ground. Several of these natural WR materials have been applied outside of their biological context and demonstrated powerful actuations with energy densities ranging from 8 kJ m$^{-3}$ to 21.3 MJ m$^{-3}$, which has enabled various applications, including macroscopic machines that are driven by evaporation energy. While nature continues to provide inspiration for the development of WR materials, the fundamental actuation mechanisms are not yet understood across the molecular to macroscopic length scales, thus hampering rational design and improvement of these materials.

The best-performing examples share a number of characteristics: they consist of both rigid nano-crystalline regions that are inter-dispersed with less-ordered amorphous (reconfigurable) regions; they typically contain repetitive sequences of hydrophilic and hydrophobic segments that strongly interact through supramolecular interactions; and they consist of hierarchical and porous architectures with high mechanical strength and toughness. Notably, the multi-scale, hierarchical organization and amphiphilic aspects have been effectively exploited in synthetically derived WR actuators.

At the most fundamental level, a material's water-responsiveness is an energy conversion process that involves absorption and desorption of water molecules which is driven by the chemical potential difference between water bound to the material and that in the surrounding atmosphere. Hydrogen bonding and water-surface interactions, as well as reversible, non-covalent interactions within the material's structure are believed to be essential to their energy conversion processes in order to translate molecular interactions to material level deformations.

The discussion above is merely provided for general background information and is not intended to be used as an aid in determining the scope of the claimed subject matter.

SUMMARY

This disclosure provides a thin film that has a flexible polymer layer and a peptide layer. The peptide layer is disposed on the flexible polymer layer and has a peptide selected from HYF, DYF and YFD. The thin film reversibly curves with changes in humidity.

In a first embodiment, a thin film is provided. The thin film comprising: a flexible polymer layer; and a peptide layer comprising a peptide, wherein the peptide layer is disposed on the flexible polymer layer, the peptide being selected from a group consisting of HYF, DYF and YFD.

This brief description of the invention is intended only to provide a brief overview of subject matter disclosed herein according to one or more illustrative embodiments and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3D shows representations of the change in the internal pore volume for HYF. The change in the area for each cross section was determined through the decrease in the average pore width.

FIG. 3E shows representations of the change in the internal pore volume for DYF. The change in the area for each cross section was determined through the decrease in the average pore width.

DETAILED DESCRIPTION OF THE INVENTION

This disclosure provides a thin film that comprises a flexible polymer layer with a peptide layer disposed on, and contiguous with, the flexible polymer layer. The peptide layer comprises crystals of a peptide selected from HYF, DYF and YFD. Suitable flexible polymers include polyimides, a polyethylene terephthalate sold under the brand name MYLAR®, polymerized siloxanes (silicone), polydimethylsiloxane (PDMS), silk, latex rubber, natural rubber, and polycarbonate (PCTE). The flexible polymer layer may have a thickness between 2 μm and 5 mm. In another embodiment, the flexible polymer layer may have a Young's moduli between 100 kPa and 10 GPa. The peptide layer may have a thickness between 0.5 μm and 1 mm. In another embodiment, the peptide layer may have a Young's moduli between 100 kPa and 10 GPa.

The thin films disclosed herein have a variety of commercial applications. For example, the thin films may be used as an actuating component for various engineering applications, such as artificial muscles, robotics, origami structures, smart structures, shape-morphing, underwater actuations, submerged vehicles, and exoskeletons. For example, the thin films could provide greater than 100 MPa actuation pressure and a fast actuation rate (less than 1 s per stroke) by injecting low pressure dry or humid air, providing new opportunities for untethered robots and exoskeletons. The thin films may also be used as water-responsive materials in the rotary engine of U.S. Patent Publication US2019/0309735.

Figure 1A:
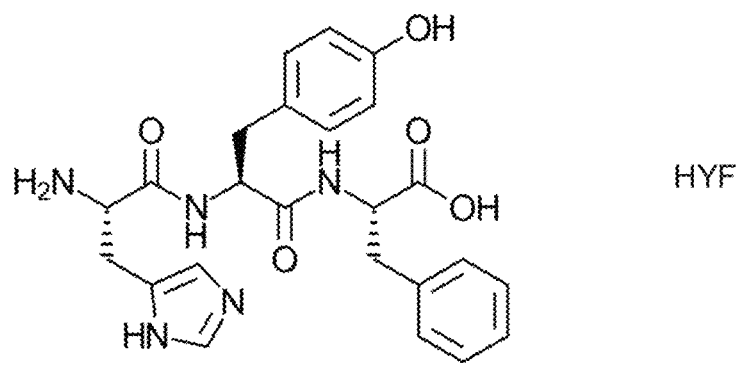
FIG. 1A depicts the chemical structures of HYF, DYF, and YFD.
Figure 1A:
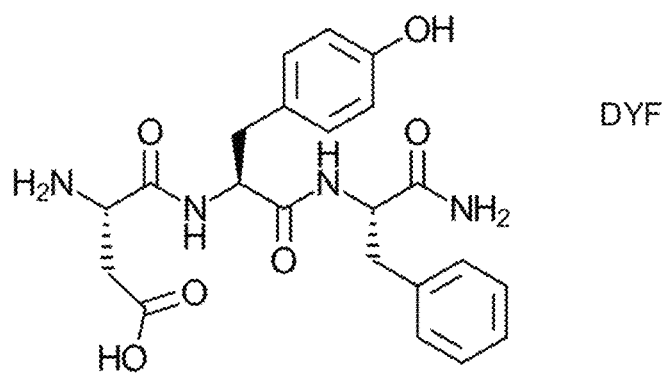
Figure 1A:
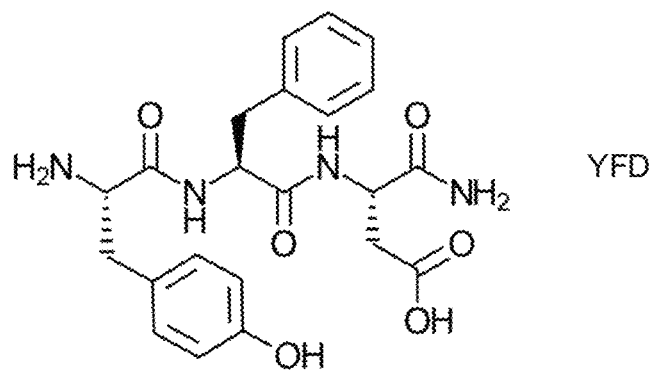
Figure 1B:
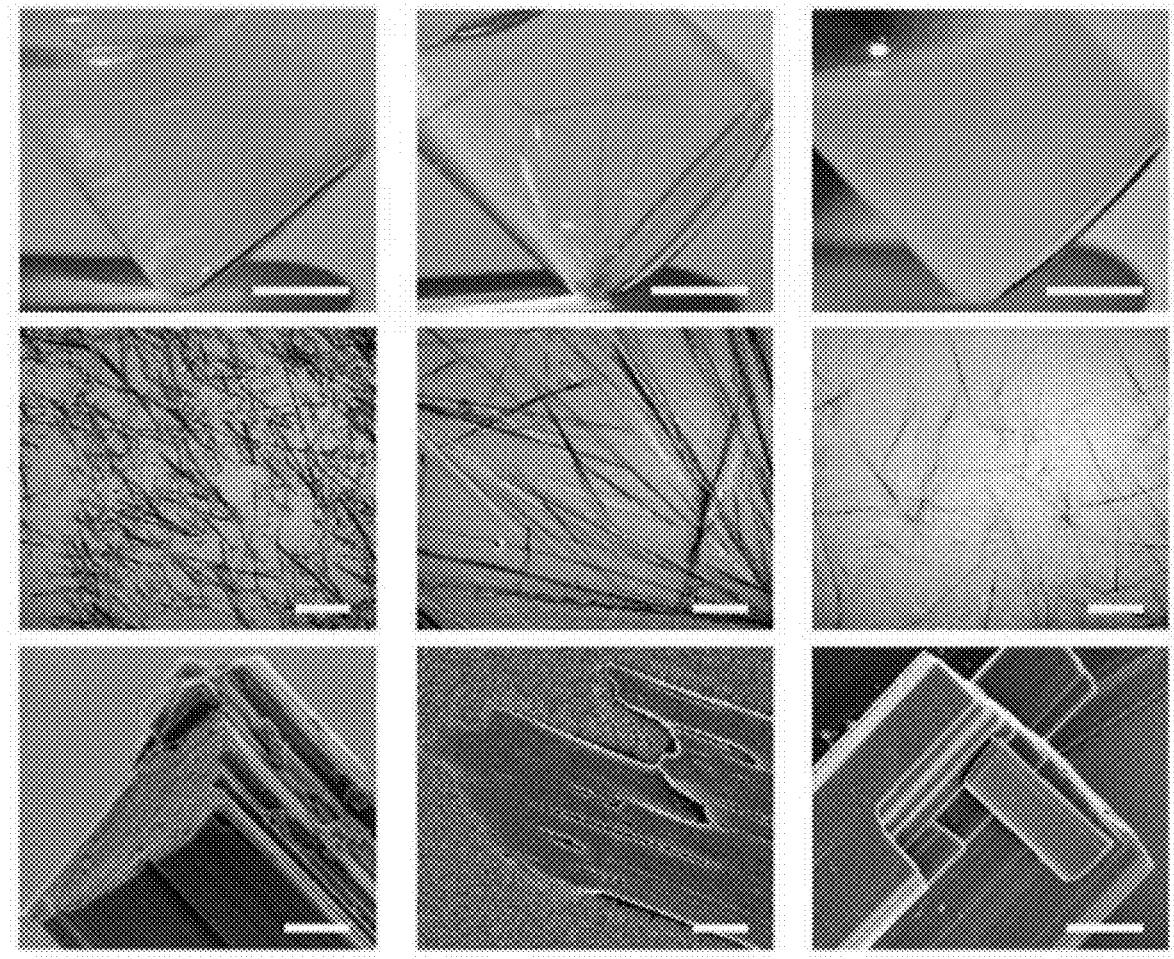
FIG. 1B depicts the tripeptides from FIG. 1A crystallized in phosphate buffer (PB) at pH 8, scanning electron microscope images (scale bar, 2 μm) of HYF, DYF, and YFD crystals.

Initially, several tripeptide sequences were selected that comprise dyads of aromatic residues—tyrosyl-phenylalanine (YF), complemented with amino acids histidine (H) or aspartic acid (D) to favor interactions with water; namely HYF, DYF and YFD (FIG. 1A). [DYF and YFD were amidated at the carboxyl-terminus (C-terminus) to enhance their aqueous aggregation propensity]. HYF, DYF, and YFD form needle-like crystals in a buffered solution within minutes (FIG. 1B, and Methods).

Figure 1C:
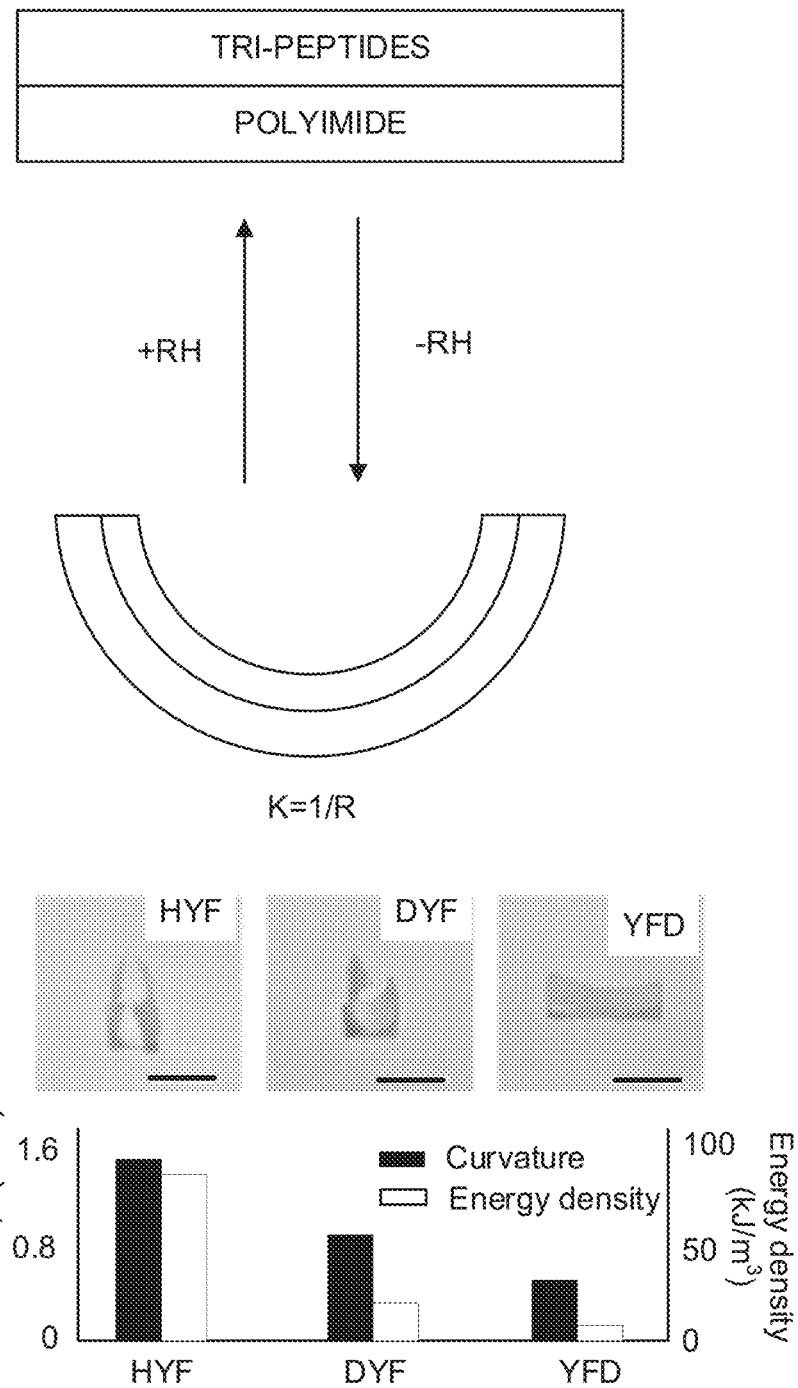
FIG. 1C depicts crystal-coated polyimide films reversibly curve and straighten in response to RH changes (scale bar, 2 mm).
Figure 1D:
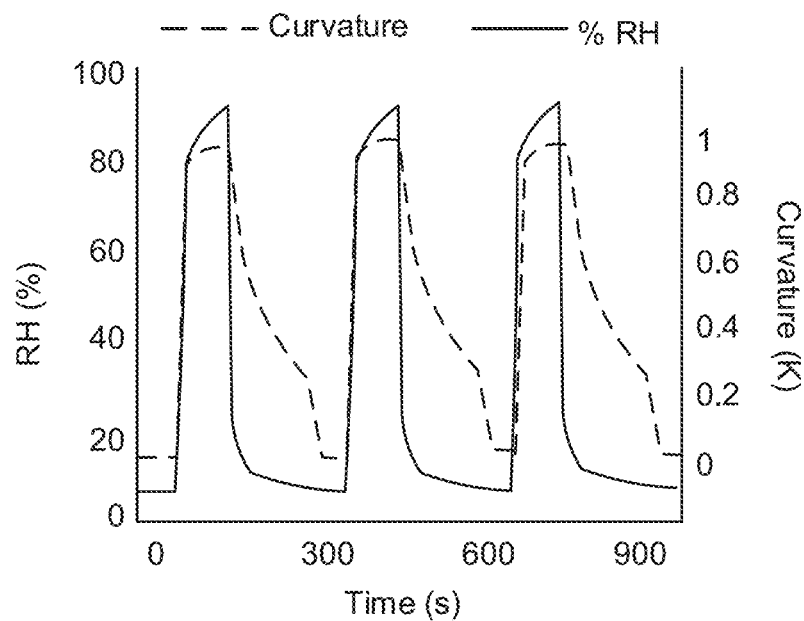
FIG. 1D and FIG. 1E show the WR actuation behavior of HYF coated polyimide film in response to alternating humidity and its hydration and dehydration speed.
Figure 1E:
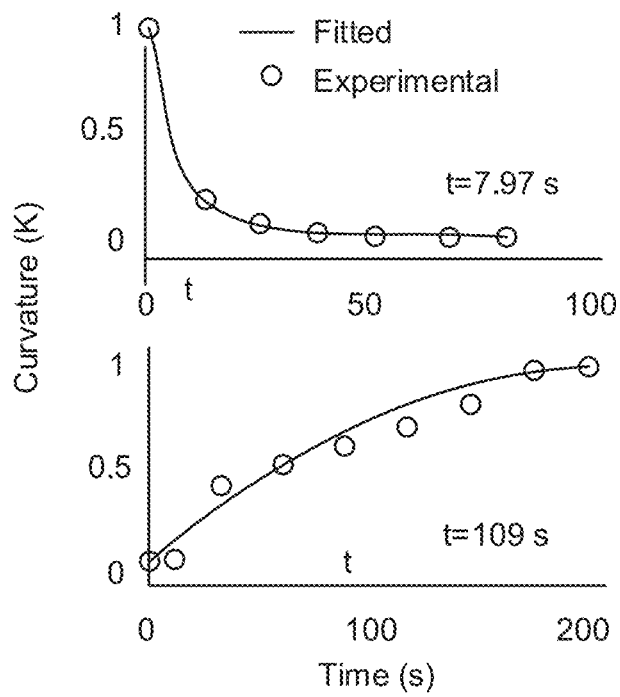

To test the WR behavior of these crystals in a macroscale experiment, a polyimide film was coated with a crystal/adhesive composite—see Methods for details of composite and film construction (FIG. 1C). Upon periodically alternating RH, polyimide films with HYF and, to a lesser extent DYF, can reversibly bend, while YFD responds only weakly (FIG. 1C and FIG. 1E). Based on maximum curvatures of polyimide films, the WR actuation energy density of these HYF, DYF, and YFD crystals is estimated to be ~88 kJ m$^{-3}$, ~18 kJ m$^{-3}$, and ~5 kJ m$^{-3}$, respectively, demonstrating clearly that peptide sequence strongly influences WR behavior.

Figure 1F:
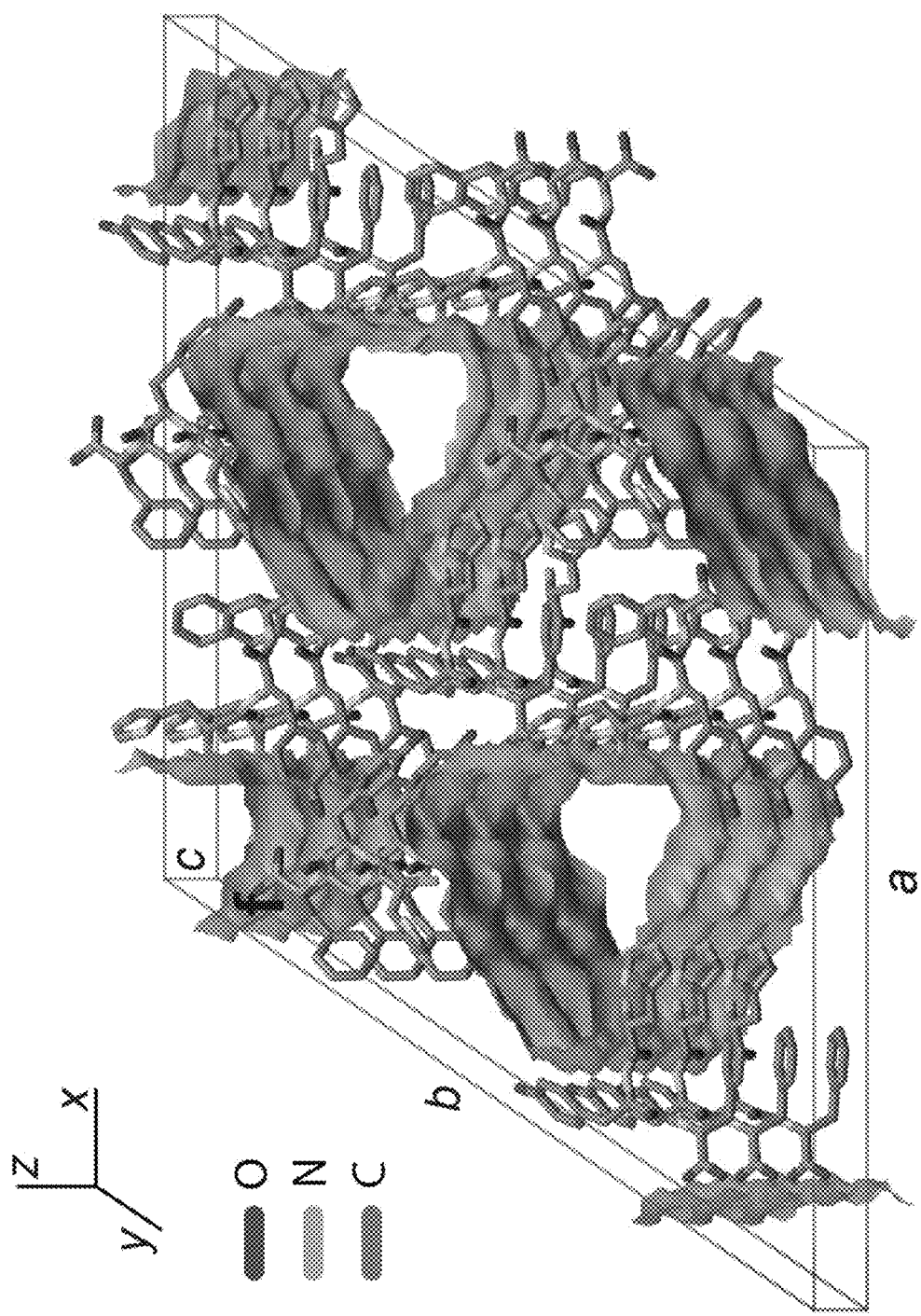
FIG. 1F shows HYF exhibits a rhombohedral crystal structure with intrinsic trigonal aqueous pores. Edge length of ~15.2 Å, pore volume is 2062 Å$^3$, corresponding to 28.3% of the unit cell volume.
Figure 1G:
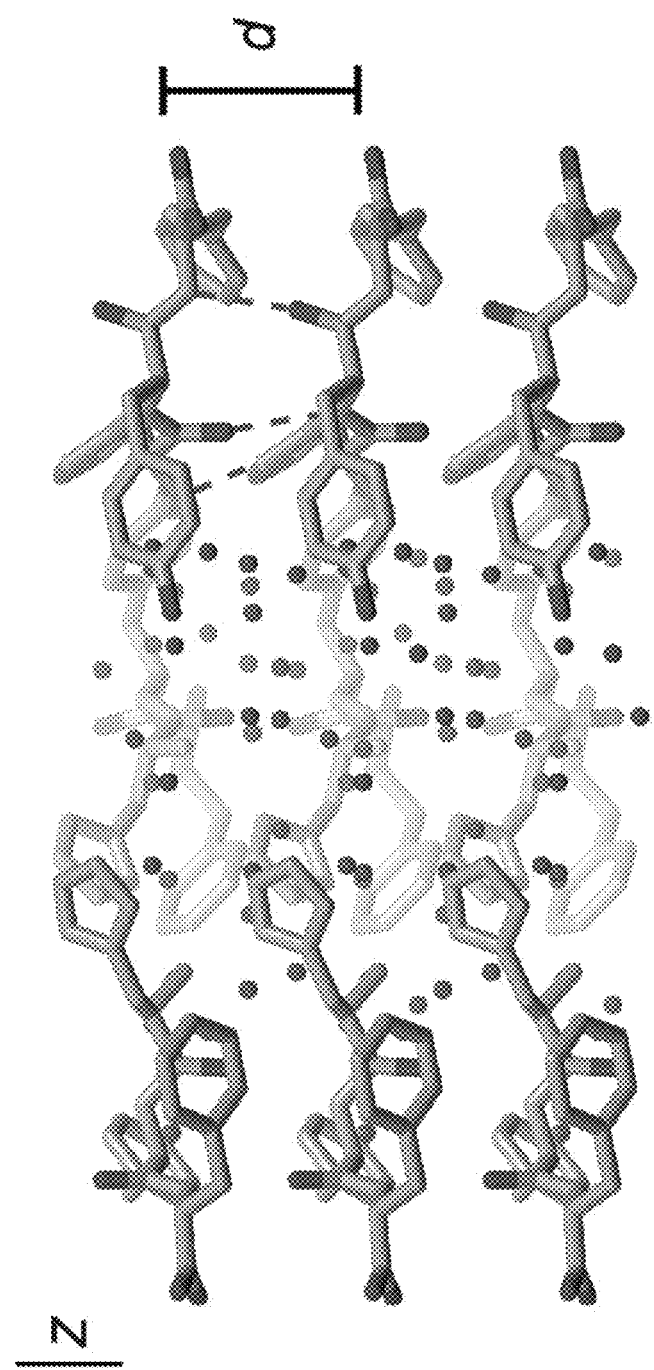
FIG. 1G is a cross-section view of FIG. 1F shows that tripeptides are arranged through H-bonding and aromatic stacking in the z-direction, and the distance d between layers in hydrated state is 4.951(6) Å.
Figure 1H:
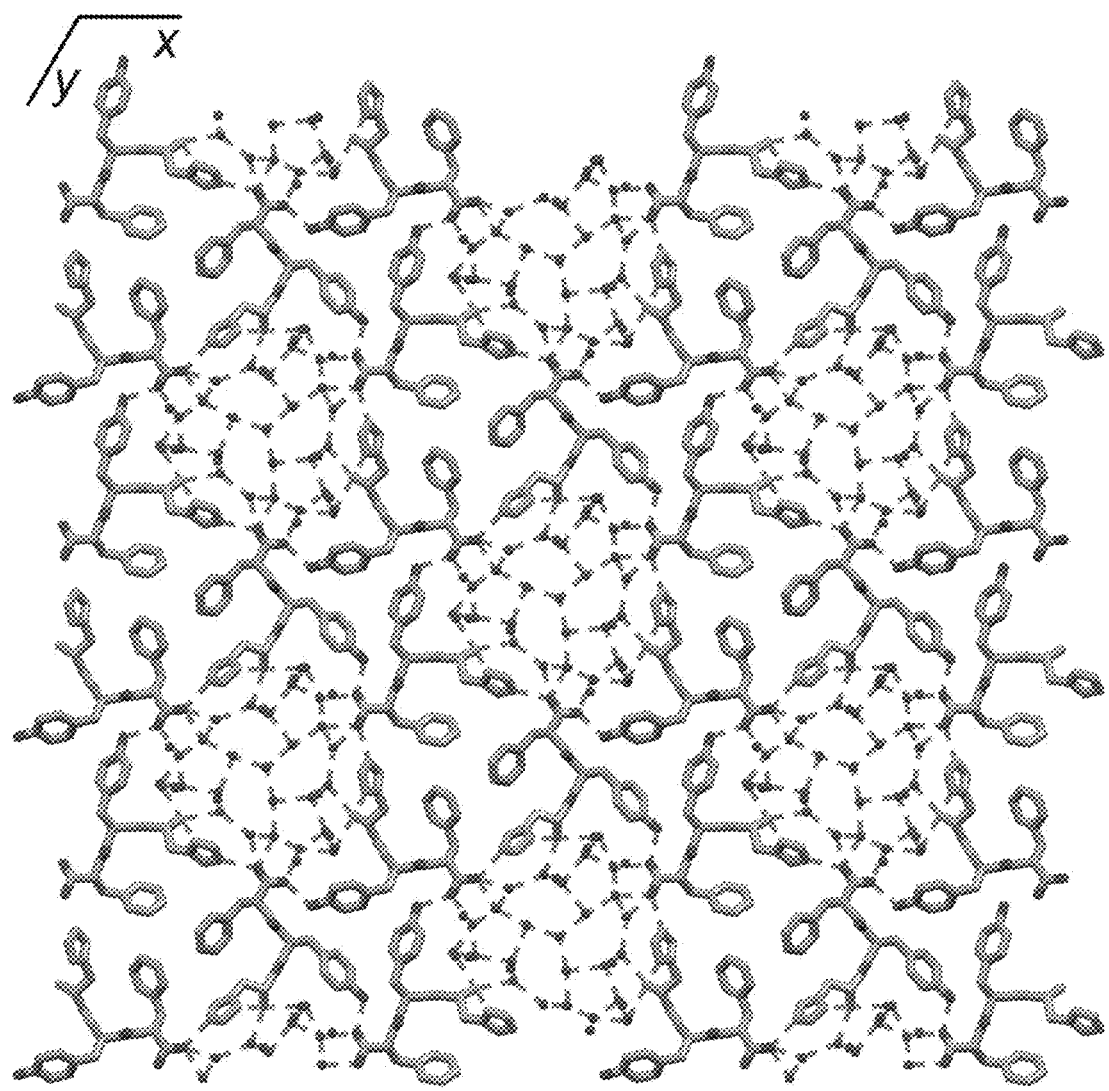
FIG. 1H is a top view showing tripeptide molecules are interacting though H-bonding and structured water molecules in the xy-plane.

Tripeptide crystals exhibit water-containing pores of varying size, and further exhibit variable supramolecular organization of peptide components within the crystal lattice. HYF's crystal structure was determined using single-crystal X-Ray diffraction (SC-XRD) (see Methods) with the crystal structures of DYF and YFD reported previously. The crystal structure of HYF was found to be rhombohedral, with lattice parameters a=b=41.202(5) Å, c=4.951(6) Å, α=β=90°, and γ=120° (FIG. 1F). HYF crystals form parallel and triangular-shaped pores (28.3% of the unit cell volume) that contain water molecules with differing degrees of bonding and mobility (FIG. 1F and FIG. 1H). In the xy-plane, the network is stabilized by H-bonding between the tyrosine hydroxyl and the C-terminus and between water molecules and both the amino-terminus (N-terminus) and the C-terminus around the aqueous pores (FIG. 1H). Tripeptide molecules further interact through H-bonding, aromatic stacking, and electrostatic interactions in the z-direction (FIG. 1G). The areas between the pores show clusters of phenylalanine side chains which are readily deformable through aromatic slippage.

In contrast to HYF, previously reported DYF and YFD are both monoclinic systems. Tripeptide conformations and water inclusion within these crystals are substantially different. Specifically, within YFD, the N-terminus forms an intramolecular salt bridge with the aspartic acid side chain and the phenol/phenyl pair of YF form an intramolecular it-stack. This leads to less intermolecular connectivity and thus reduced water-responsiveness of YFD crystals. Beyond differences in intermolecular connectivity within the crystals, chemical structure and geometry of the aqueous pores also varies, which results in differential water-occupancy (FIG. 1F). Compared to DYF, the ability of HYF to accommodate both ordered and disordered water molecules in pores that are interspersed with deformable aromatic regions (FIG. 1H) correlates to a more significant macroscale response to changes in RH.

Figure 2A:
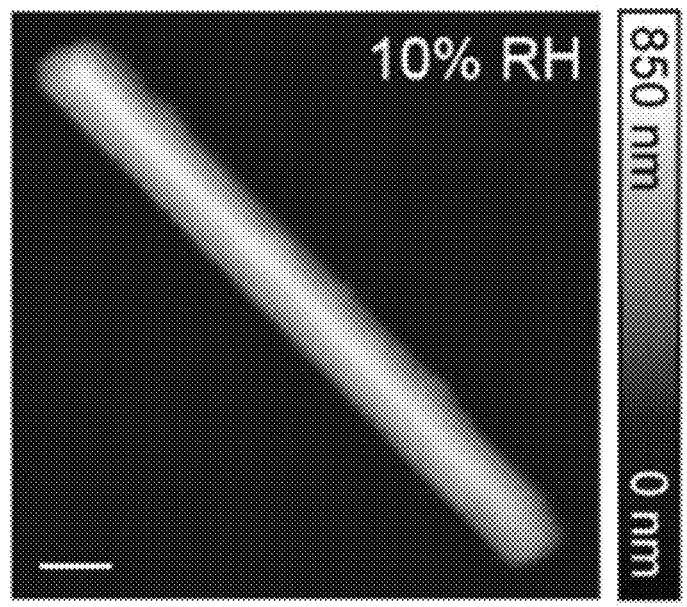
FIG. 2A is a image of a HYF crystal.
Figure 2B:
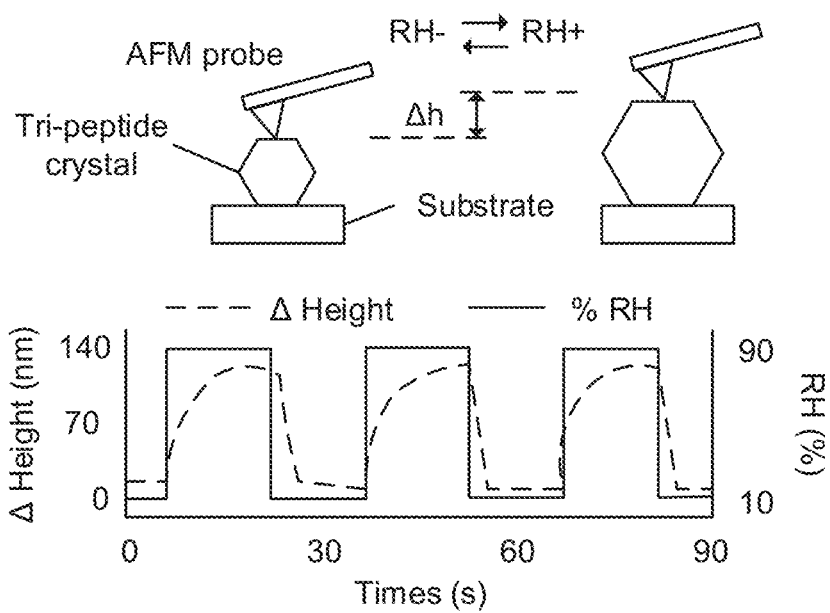
FIG. 2B depicts AFM topography measurement shows the expansion of HYF crystals. The dynamic height change was monitored while local RH was rapidly alternated between 10% and 90%.
Figure 2C:
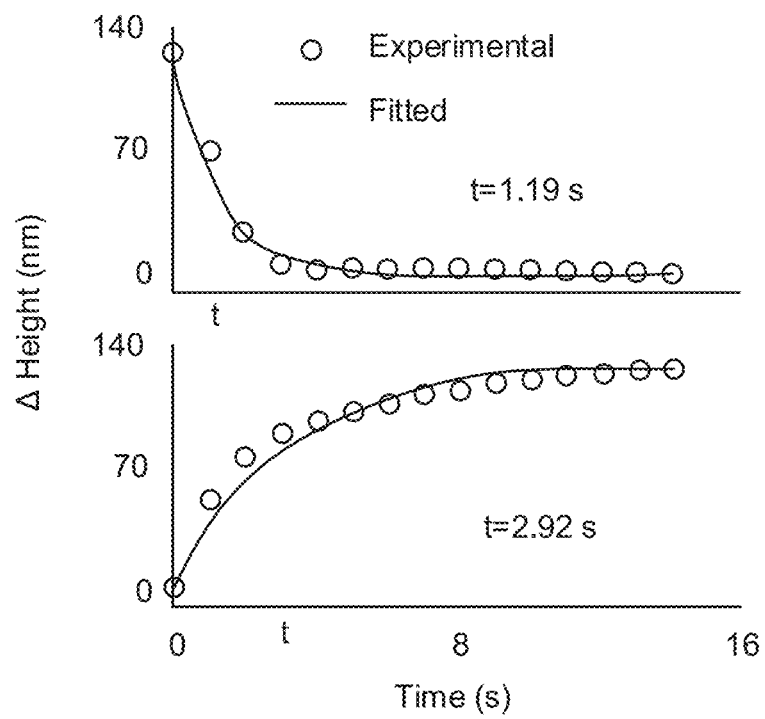
FIG. 2C shows HYF's hydration and dehydration speed.
Figure 2D:
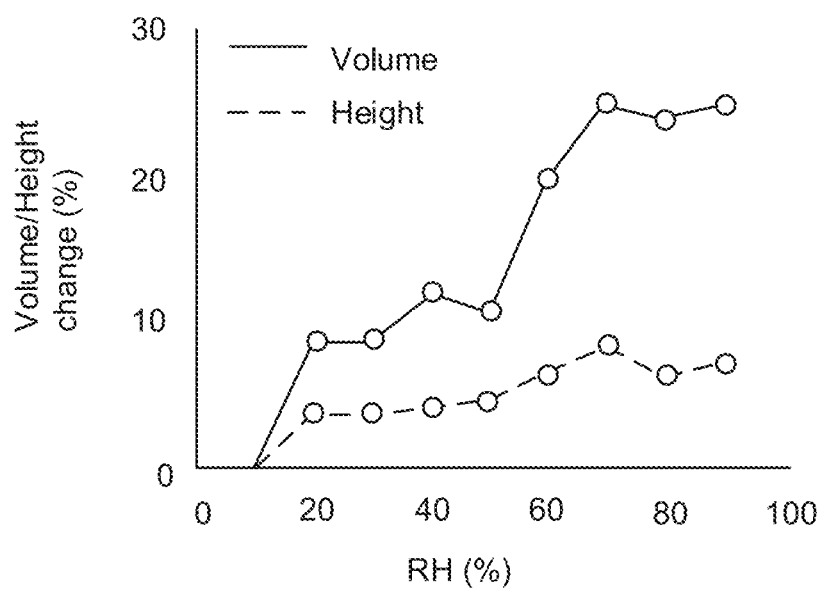
FIG. 2D illustrates volume and height vs. % RH of HYF.

A customized atomic force microscope (AFM) that allows for rapid adjustment of local RH while monitoring the topographical change was used to quantify shape changes (FIG. 2A and FIG. 2B). When the local RH is alternated between 10% and 90%, a HYF crystal of ~2 μm in width shows rapid actuation (1.2 s to expand upon hydration and 2.9 s to contract upon dehydration, (FIG. 2B and FIG. 2C). These response times are much faster compared to those of the macroscopic HYF/polyimide films (7.97 s for hydration and 109 s for dehydration, FIG. 1D and FIG. 1E). This size dependence can be explained by faster water diffusion in smaller structures and the adhesive barrier for the crystal/adhesive composites, complying with the classic Fick's law of normal diffusion. During repeated actuations, HYF crystals displayed a height change of ~8% (FIG. 2B and FIG. 2D). The micron-scale tripeptide crystal structures have asymmetric morphology, thereby resulting in a non-uniform WR strain in different dimensions (FIG. S7). Considering the size changes, HYF's volume increases ~24.6% upon hydration (HYF) (FIG. 2D), while DYF and YFD increase by ~13.9% and ~3.7%, respectively (FIG. 2F), which is consistent with the trends observed in the polyimide film deformation experiment (FIG. 1C). The micron-scale HYF crystal's actuation energy density (~6.5 MJ m$^{-3}$, see calculation details in Methods) compares well with reported values for natural materials and is higher than that observed in the macroscopic HYF/polyimide films due to the energy dissipation of the adhesive used in these films.

Figure 2E:
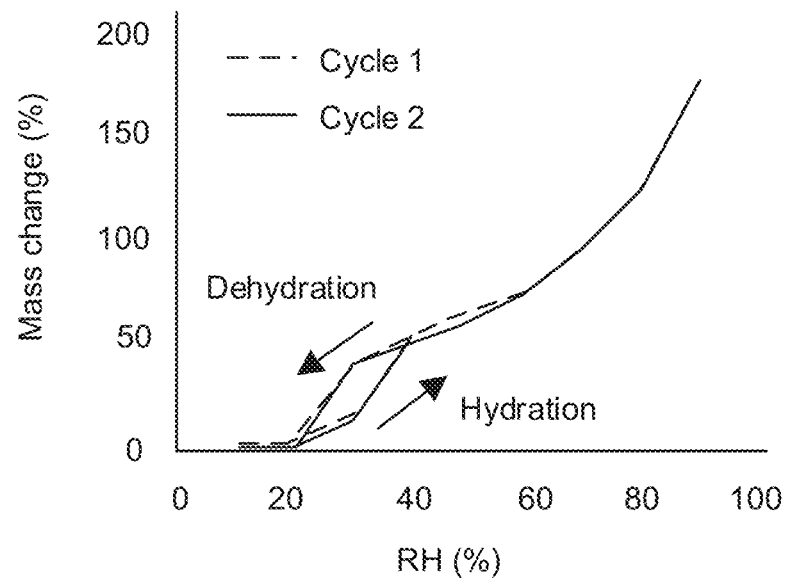
FIG. 2E is a graph showing DVS water sorption isotherms of HYF crystals. Mass change vs. RH curve show hysteresis between 20% RH and 40% RH during hydration and dehydration cycles.
Figure 2F:
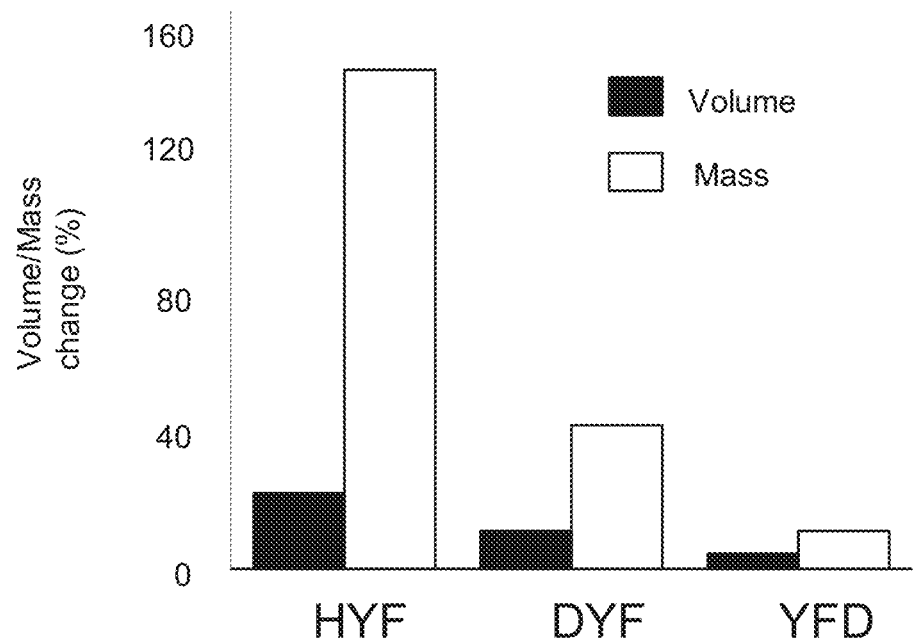
FIG. 2F is a graph showing % volume and mass change of HYF, DYF and YFD between 10% and 90% RH. The volume change in FIG. 2D is estimated from the height, width, and length changes of individual crystals.

Mass changes as a result of water absorption and desorption during hydration/dehydration cycles were investigated using Dynamic Vapor Sorption (DVS), giving 148.2% for HYF (FIG. 2E and FIG. 2F), 41.8% for DYF, and 11.3% for YFD (FIG. 2F). These results show substantially more water uptake than the volume expansions which were determined by AFM suggest. These differences are related to water adsorption at the next hierarchical level, i.e., on crystal surfaces and interfaces between aggregated crystallites, which are also visible by SEM and evidenced by the hysteresis loop of water sorption isotherms analyzed using the Young-Nelson (YN) model (FIG. 2E).

Figure 2G:
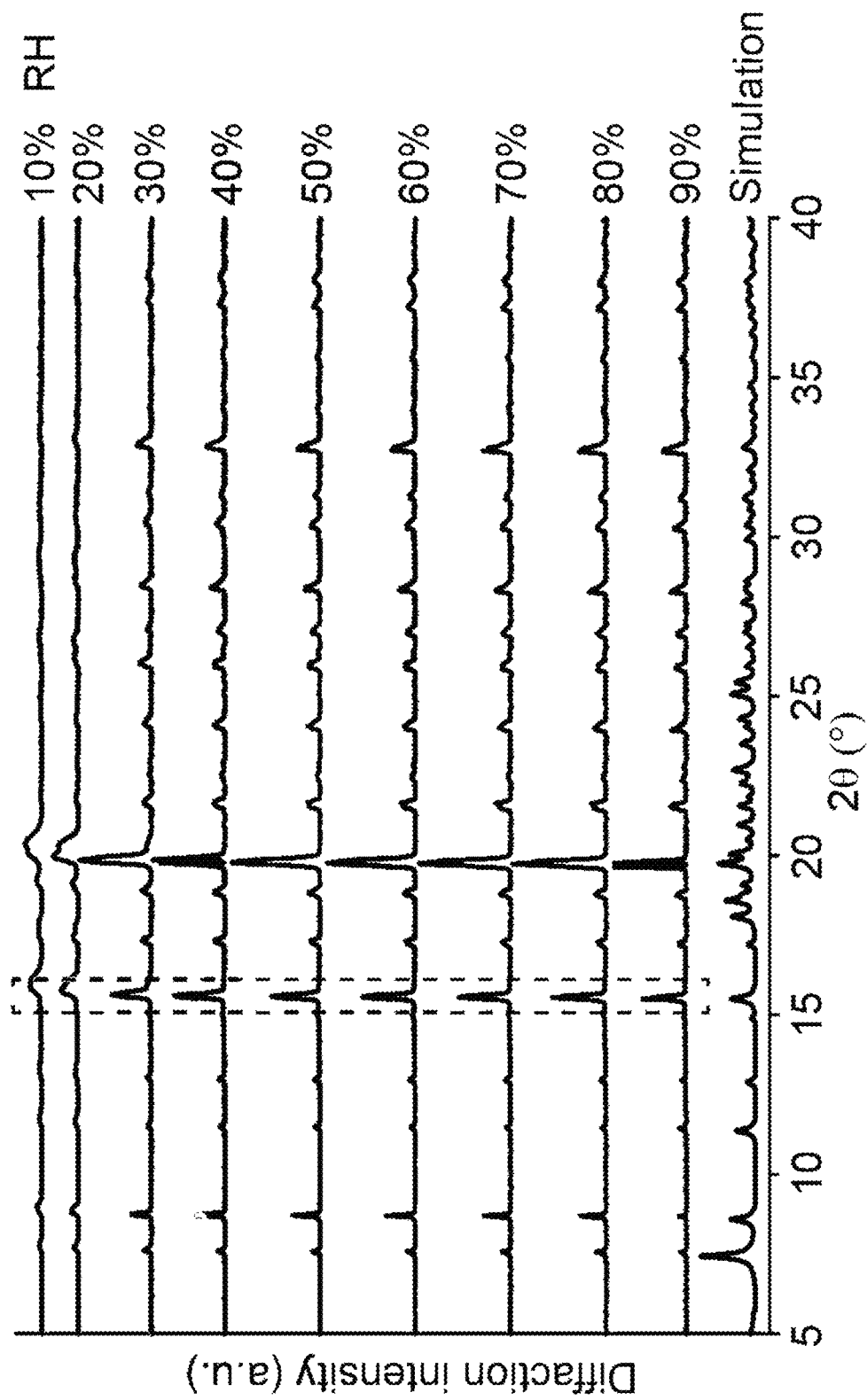
FIG. 2G depicts a PXRD graph showing diffraction pattern changes upon rehydration.
Figure 2H:
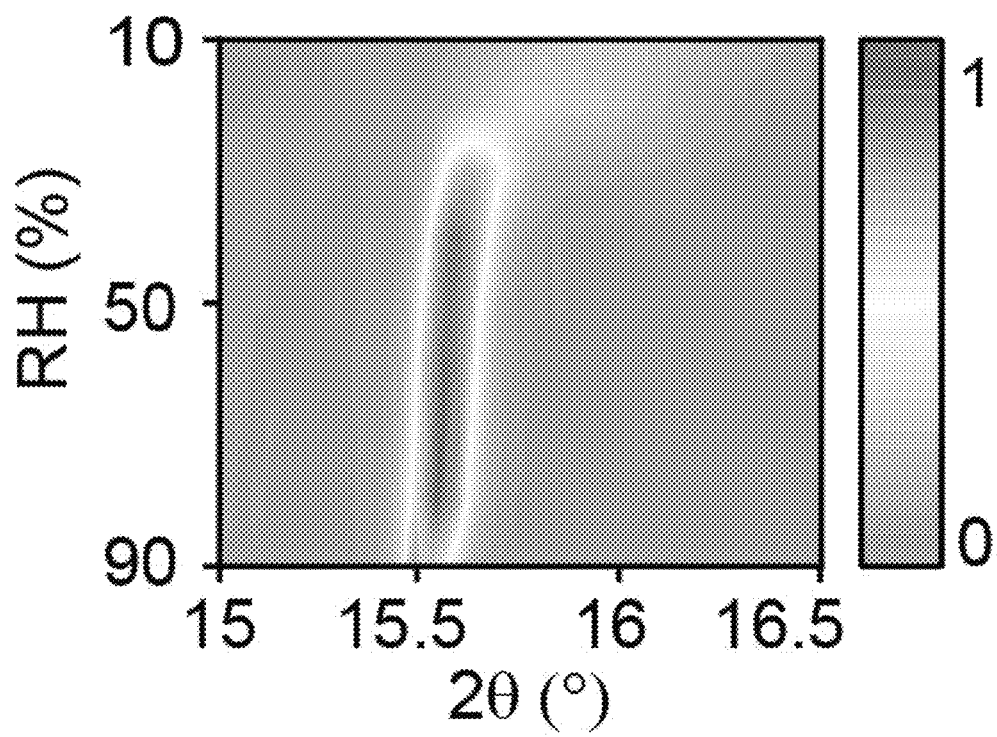
FIG. 2H is a zoom-in of (750) plane diffraction indicating shift towards higher 2θ values.

To understand how changes in the RH affect the peptide scaffold, powder X-ray diffraction (PXRD) was performed within a T/% RH environment-controlled chamber to observe the water induced lattice deformation (see Methods). For HYF crystals, since the stacking distance d is relatively short (FIG. 1G), the majority of diffracting planes of 2θ from 5' to 40° are parallel to the z-direction (FIG. 1G and Methods). During the dehydration processes, the diffraction peaks from polycrystalline HYF samples show a general shift to higher angles (FIG. 2G and FIG. 2H), which is consistent with shrinkage of the lattice as the size of water pores is reduced. When RH is further decreased to 20%, major peaks lose their intensity and broaden considerably, which suggests a sudden phase change of HYF crystals. This abrupt change at ~20% RH also correlates to the size and mass changes observed in AFM and DVS experiments (FIG. 2B, FIG. 2C, FIG. 2D, FIG. 2E, and FIG. 2F). In contrast, DYF crystals' diffraction pattern shows only minor shifts, and YFD permanently loses its original crystalline structure. Both HYF and DYF crystals fully regain their original diffraction patterns upon rehydration.

Figure 2I:
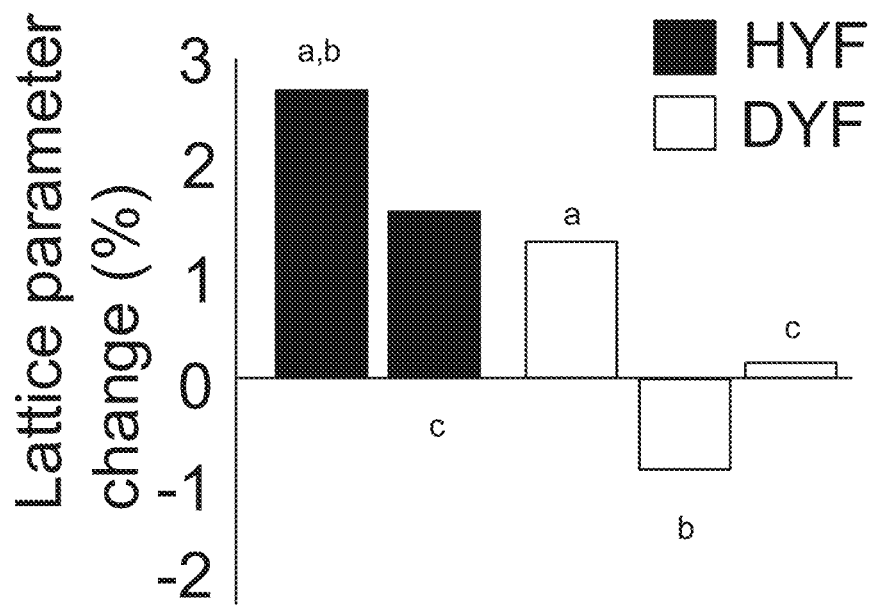
FIG. 2I is a graph of % lattice parameter changes of HYF and DYF between 10% and 90% RH from Rietveld refinement of the PXRD data.

The lattice parameter changes of HYF and DYF were calculated from a Pawley refinement of the individual PXRD diffraction patterns at each RH (FIG. 2I). The refined cell parameters confirm that the HYF crystal's unit cell volume reduces by 7.5% as % RH decreased from 90% to 10%. However, the AFM measurements show more than a 20% change in volume (FIG. 2D), which indicates that the tripeptide's polycrystalline structures and the non-uniformly orientated crystallites further amplify its lattice deformation (FIG. 1F).

Figure 3A:
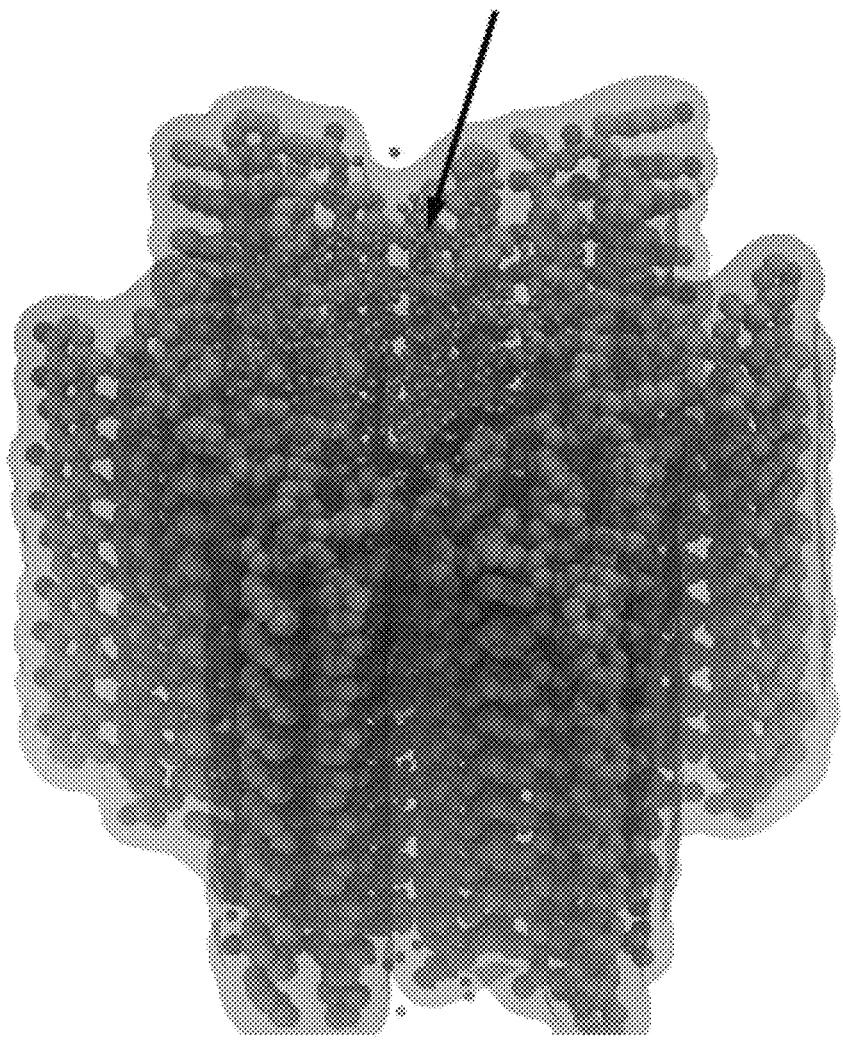
FIG. 3A shows a MD simulated crystal structure on an aqueous pore structure of HYF crystals at 90% RH.
Figure 3B:
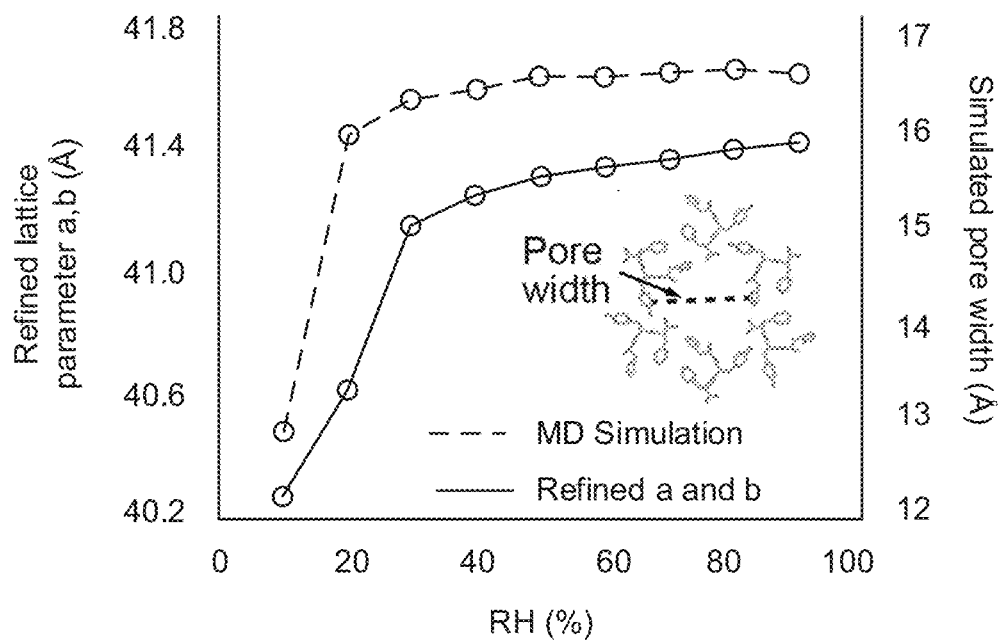
FIG. 3B is a graph comparing lattice parameter changes a/b derived from the Pawley refinement with MD simulated pore width in response to RH (R. Hyd.) changes for HFY.
Figure 3C:
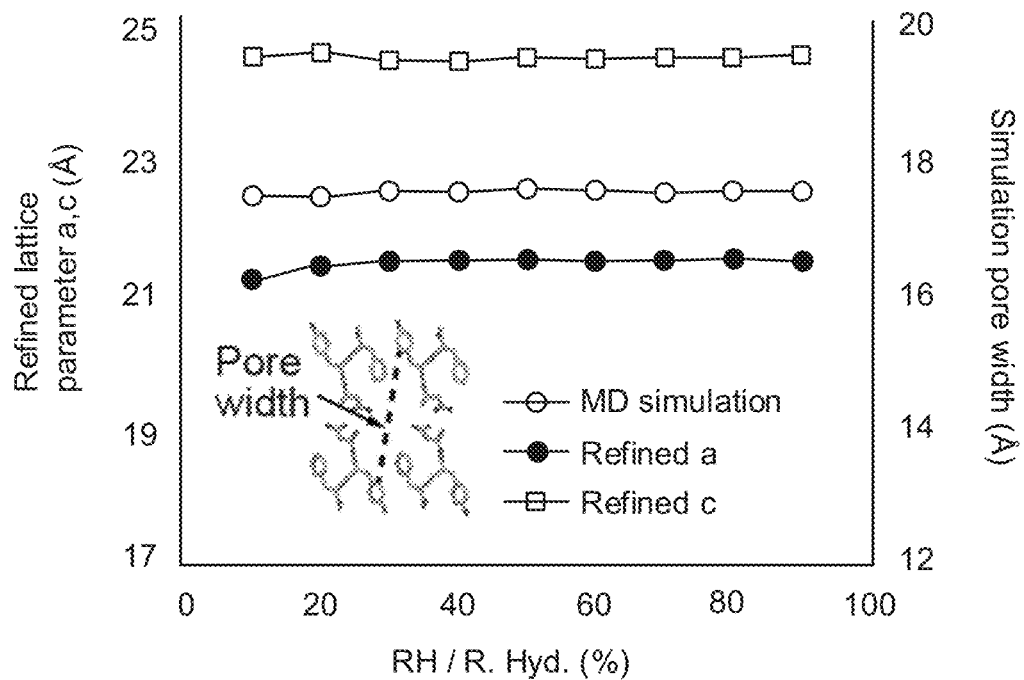
FIG. 3C is a graph comparing lattice parameter changes a/b derived from the Pawley refinement with MD simulated pore width in response to RH (R. Hyd.) changes for DYF.

The reversible phase transitions for HYF and DYF were further investigated using Molecular Dynamics (MD) simulations (see FIG. 3A, FIG. 3B, FIG. 3C, FIG. 3D and FIG. 3E and Methods). The simulated changes in pore dimensions agree with observed changes in lattice parameters (a and b) from the Pawley refinement, which shows a dramatic shrinking and disordering of HYF pore structures starting from ~20%-30% relative hydration (R. Hyd.) as water leaves (FIG. 3B and FIG. 3D). Upon rehydration, the pore regains its original structure, owing to the HYF crystals' reversible intermolecular interactions. In contrast, DYF shows no appreciable deformation of its pore structure (FIG. 3C and FIG. 3E).

Figure 3F:
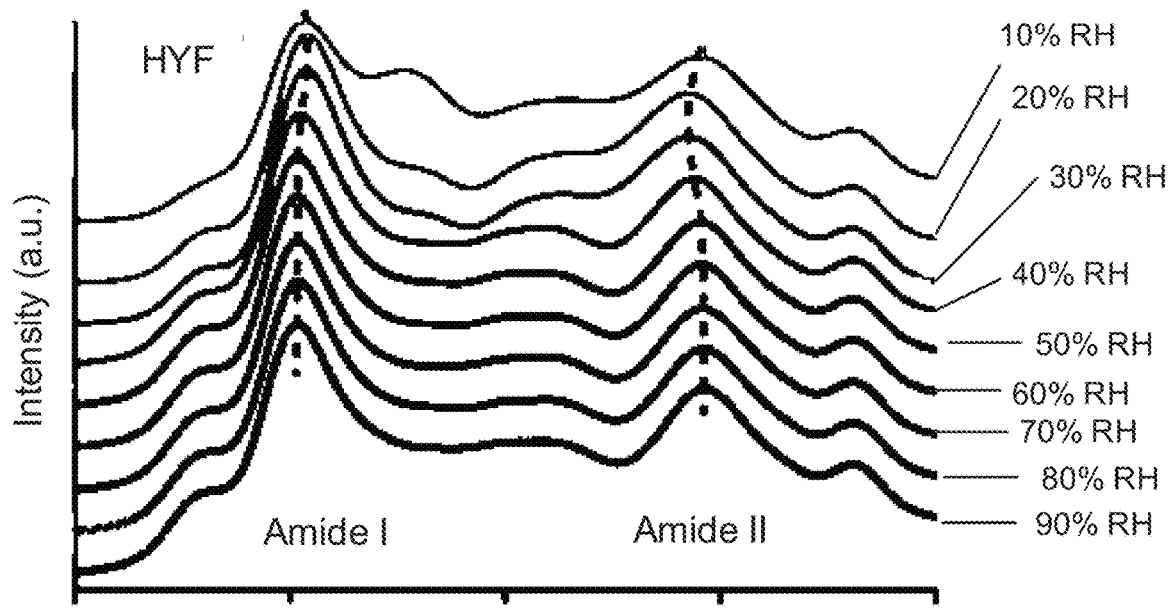
FIG. 3F shows an FTIR spectra of HYF showing that HYF's amide I and amide II bands shifting during dehydration process.
Figure 3G:
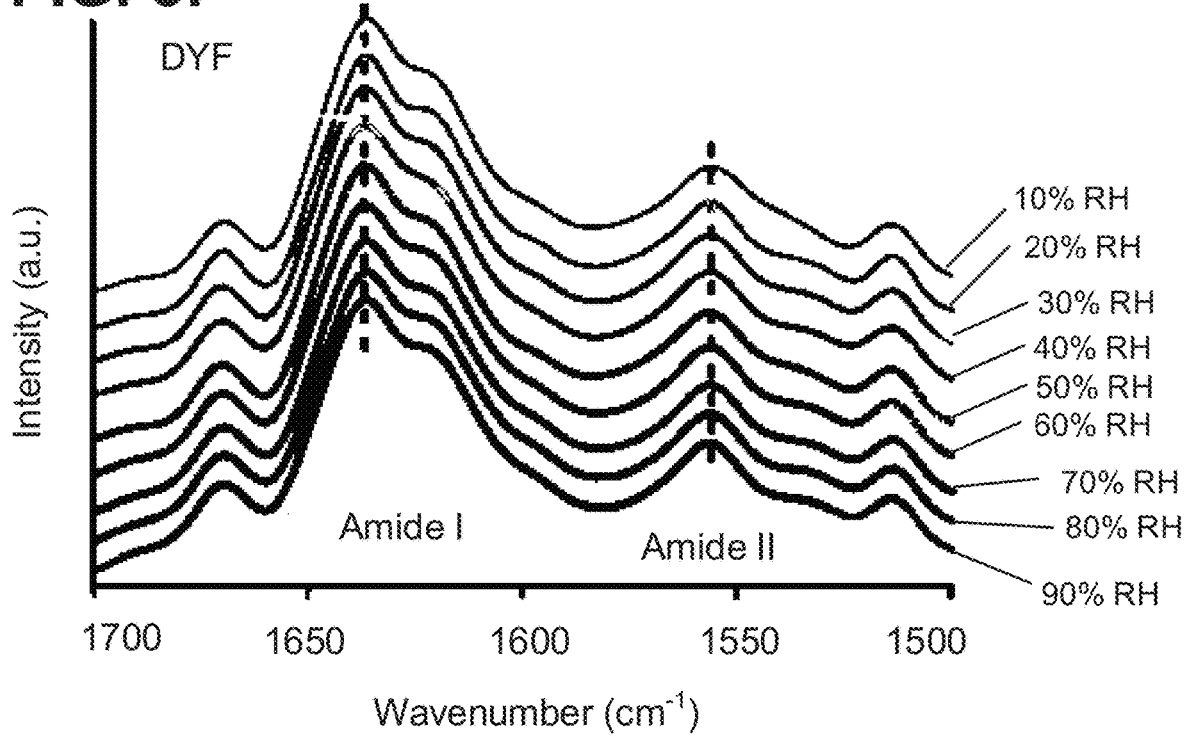
FIG. 3G shows an FTIR spectra of DYF showing that DYF's amide I and amide II bands remain unchanged.

Environmental-controlled Fourier Transform Infrared Spectroscopy (FTIR) further revealed dehydration-induced changes in intermolecular bonding interactions within the peptide structures. During dehydration, HYF crystals' amide I band shifts to a lower frequency, and the amide II band shifts to a higher frequency (FIG. 3F), indicating a strengthening in H-bonding interactions between peptides upon dehydration. This observation is consistent with the decrease in the H-bond distances that were determined by the PXRD refinement and MD simulations of the pore. As the RH drops below 20%, the H-bond lengths decrease and the overall dimensions of the pore contract (FIG. 3D). However, there were no observable changes in the amide I and amide II bands for DYF and YFD crystals (FIG. 3G), suggesting less elastic energy is transferred to DYF and YFD structures than that to HYF. Once again, this is consistent with the PXRD and MD simulations that show no effective change in the dimensions of the pore as a consequence of the decrease in RH. (FIG. 3E).

Figure 4A:
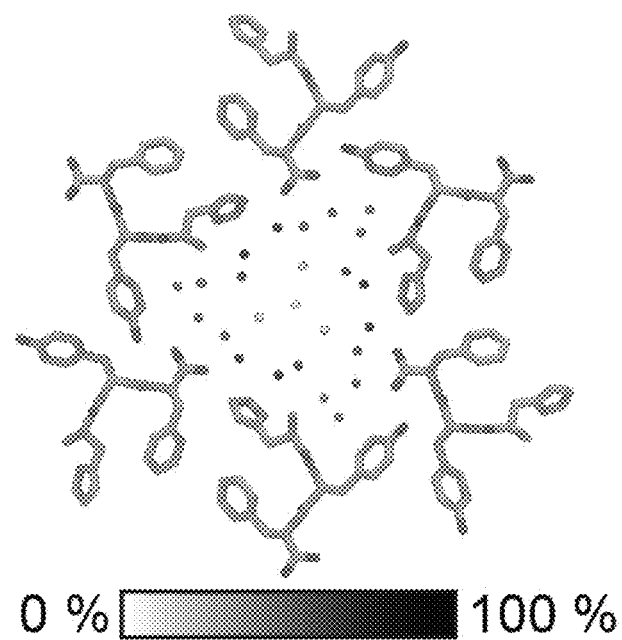
FIG. 4A shows tripeptide residues of HYF that form H bonding with water. HYF's symmetric nature of the pore results in three repeats of the same residues forming the circumference of the pore.
Figure 4B:
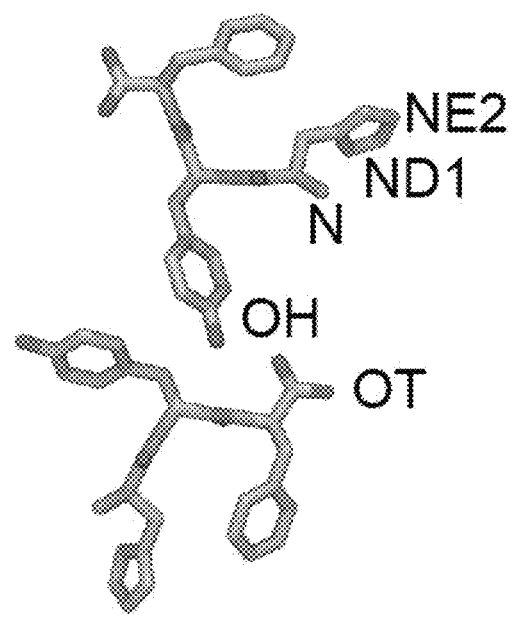
FIG. 4B is a top view of MD simulated HYF showing water molecule occupancy.
Figure 4C:
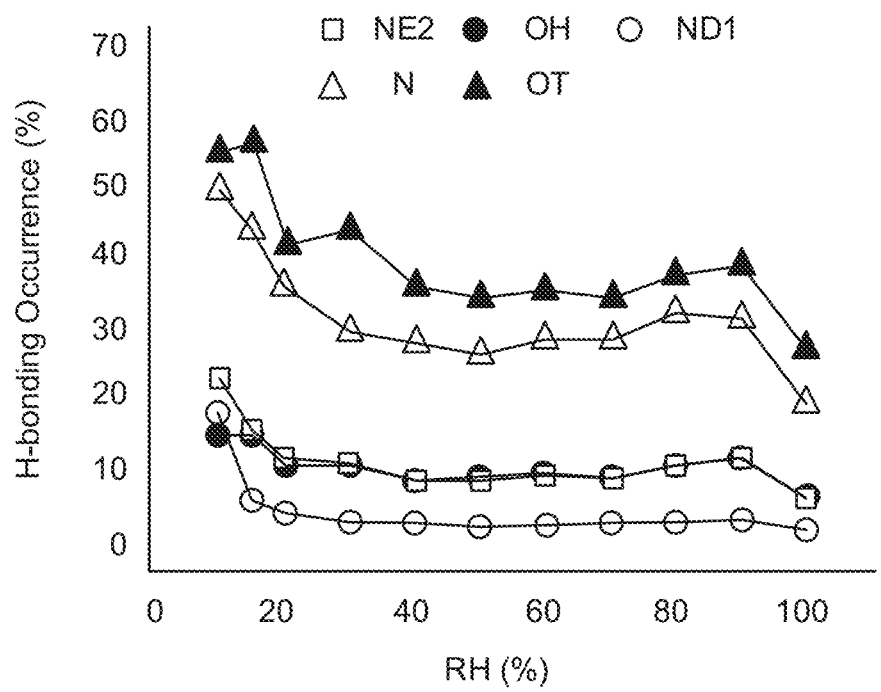
FIG. 4C is a graph depicting H-bonding occurrence in HYF.
Figure 4D:
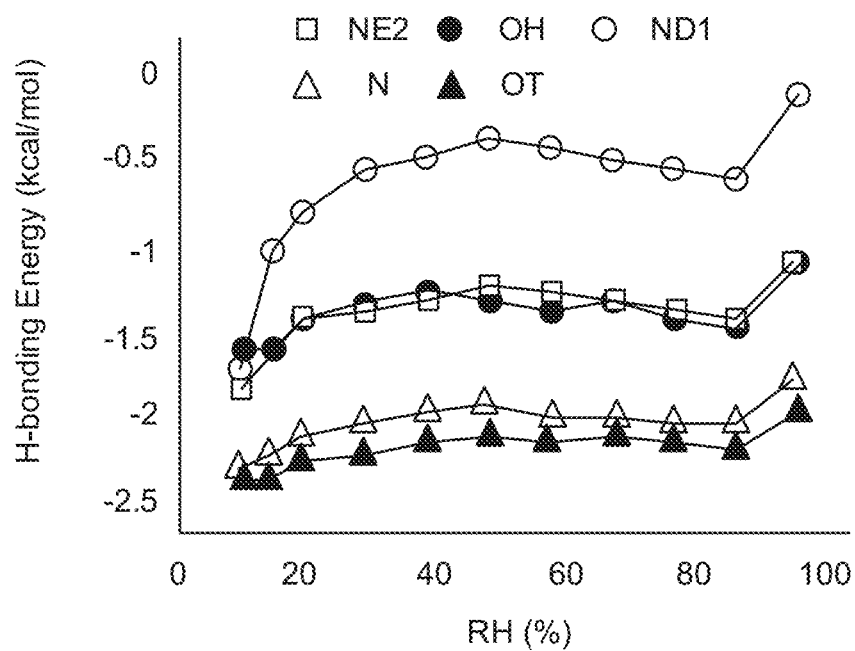
FIG. 4D is a graph depicting energy of side chains vs % RH in HYF.
Figure 4E:
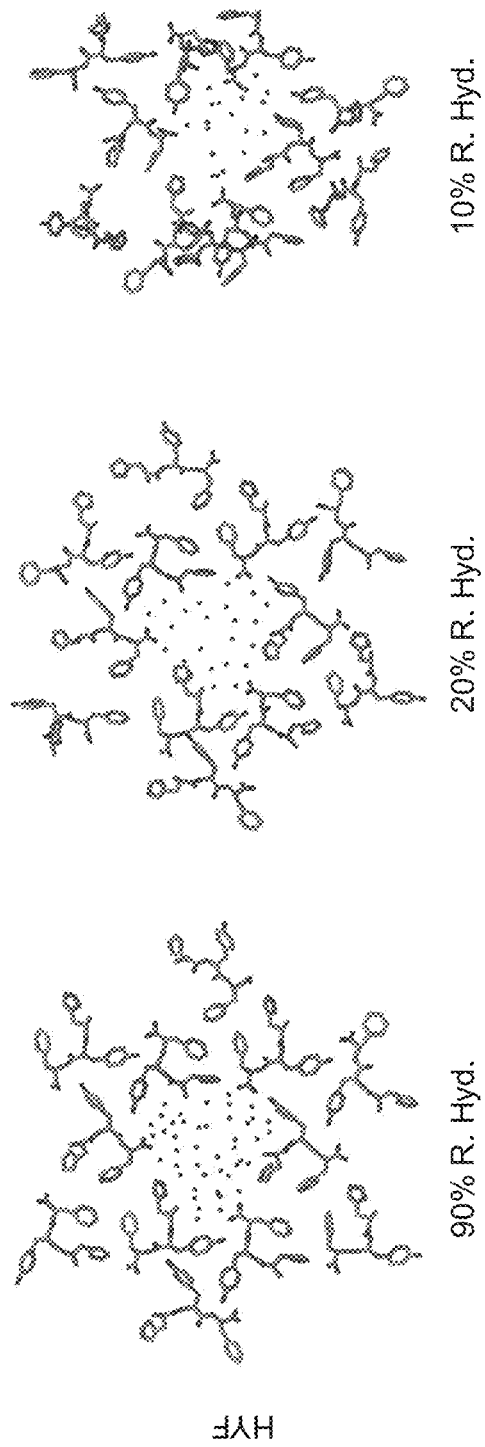
FIG. 4E provide images showing the hydrogen bonding potential of HYF with water and different RH values.
Figure 4F:
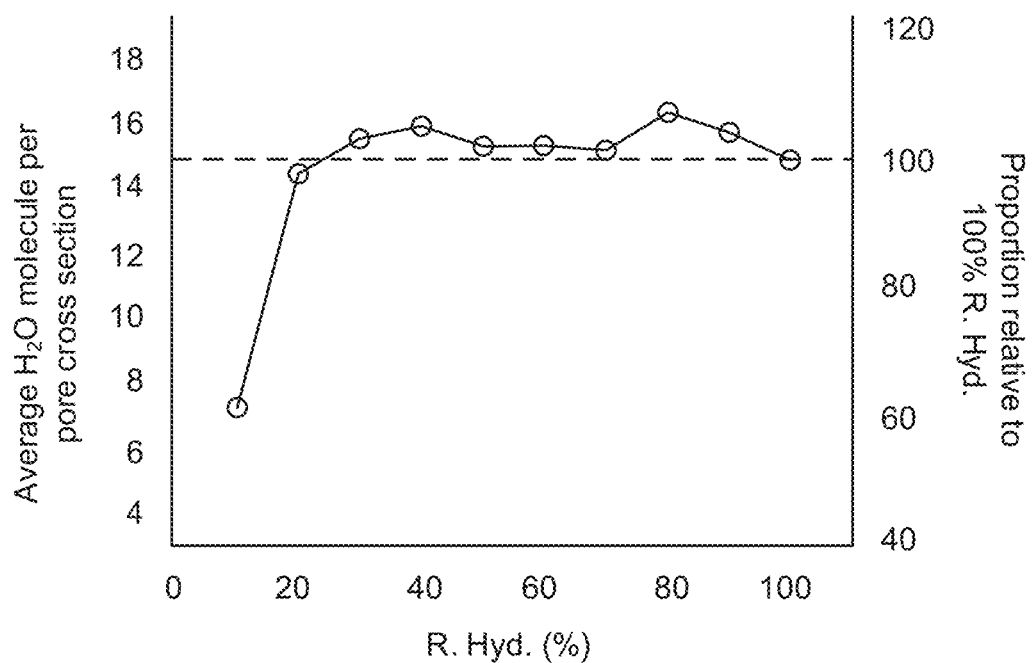
FIG. 4F shows average number of water molecules in the cross-section of the pore over the simulation frames vs. R. Hyd. for HYF.

To further understand the water-peptide interactions at the pore surface during HYF's WR expansion and contraction, the H-bond interactions between primary intrinsic water and the exposed H-bonding sites that form the surface of the aqueous pores were investigated using MD simulation (FIG. 4A, FIG. 4B, FIG. 4C, FIG. 4D, FIG. 4E, FIG. 4F and Methods). As the hydration level is decreased from 100% to 10%, paradoxically, the occupancy of the H-bonding sites dramatically increases (FIG. 4C and FIG. 4E), indicating that less water is able to exchange with pore surface H-bonding donors and acceptors and the proportional interaction energy between the water and peptide consequently increases (FIG. 4D and Methods). While water's cohesive energy generally will include multiple effects, the dominant role that H-bonding has in this process leads us to use the term H-bonding energy as a useful proxy for this study. After a ~10% increase in the H-bonding occupancy with the initial reduction in R. Hyd. from 100% to 90%, the H-bonding occupancy remains stable until ~30% R. Hyd., and finally shows a significant increase at the lowest hydration levels (FIG. 4C). This is particularly evident in the case of the terminal phenylalanine carboxylate group (OT, FIG. 4B, FIG. 4C and FIG. 4D) and the backbone nitrogen of histidine (N, FIG. 4B, FIG. 4C and FIG. 4D) in which a 20% increase in the occupation level is observed. This ability of water to bond more strongly to the nanopore surface as the hydration level decreases suggests that they are able to transfer the pressure and work done by mobilized water. This ductile structure allows the system to undergo multiple deformation cycles without compromising the internal structure of the material. This observation is confirmed by the difference between the chemical potential inside and outside the pore observed in the MD simulations. As the simulation equilibrates, water redistributes between the inside and the outside of the pore dictated by the difference in the chemical potential. This is evidenced by a comparison of the average number of water molecules in the cross-section of the pore over the simulation frames (FIG. 4F). Comparing 10% R. Hyd. to 100% R. Hyd., the overall quantity of water molecules in the system is reduced by 90%, but the average quantity of water in the pore is reduced by only around 50% as the disordered water molecules are removed from the pore and only those forming the first solvation shell of the peptide network remain, leading to a contraction of the pore (FIG. 3D).

Figures 4G, 4H:
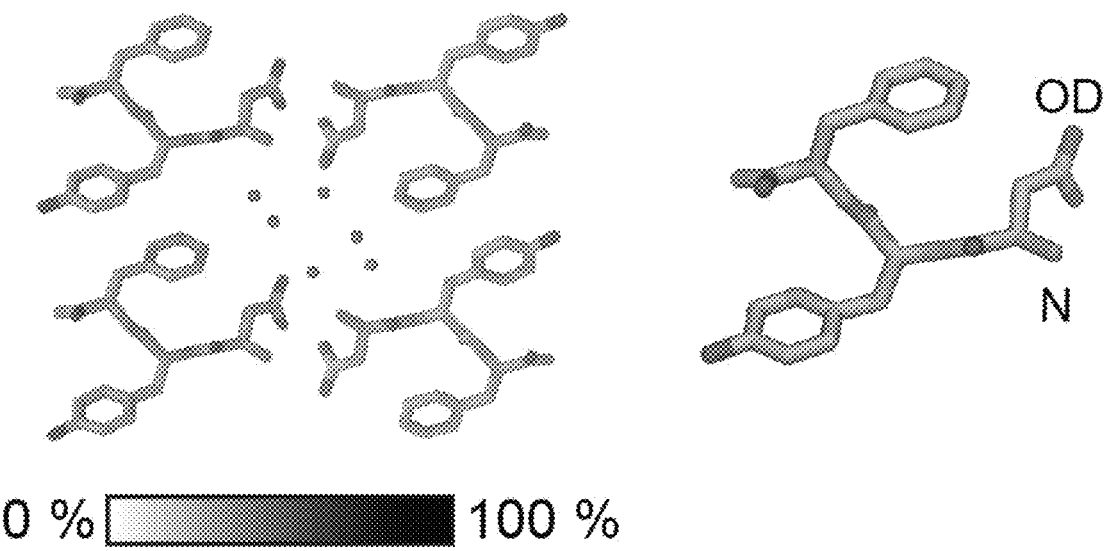
FIG. 4G shows tripeptide residues of DYF that form H bonding with water.
FIG. 4H is a top view of MD simulated DYF showing water molecule occupancy.
Figure 4I:
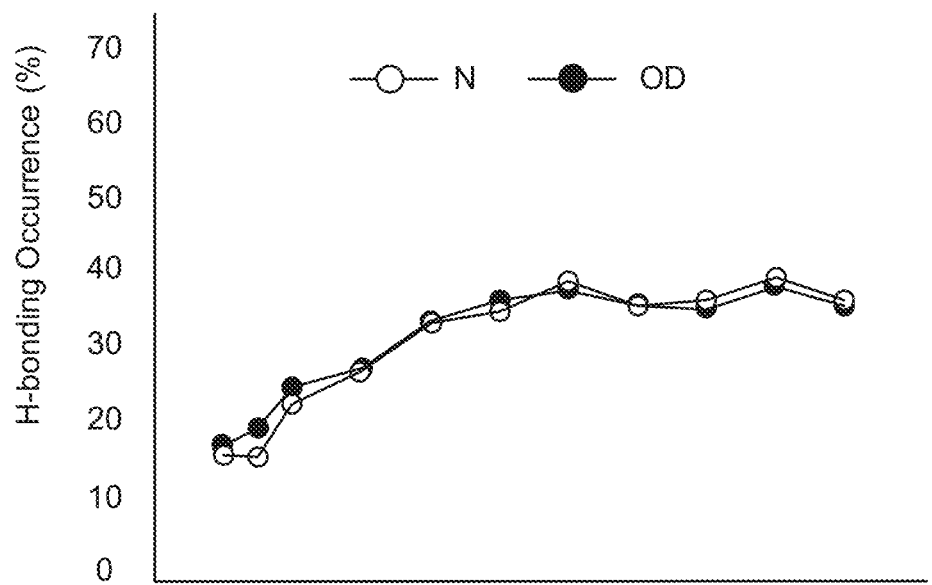
FIG. 4I is a graph depicting H-bonding occurrence in DYF.
Figure 4J:
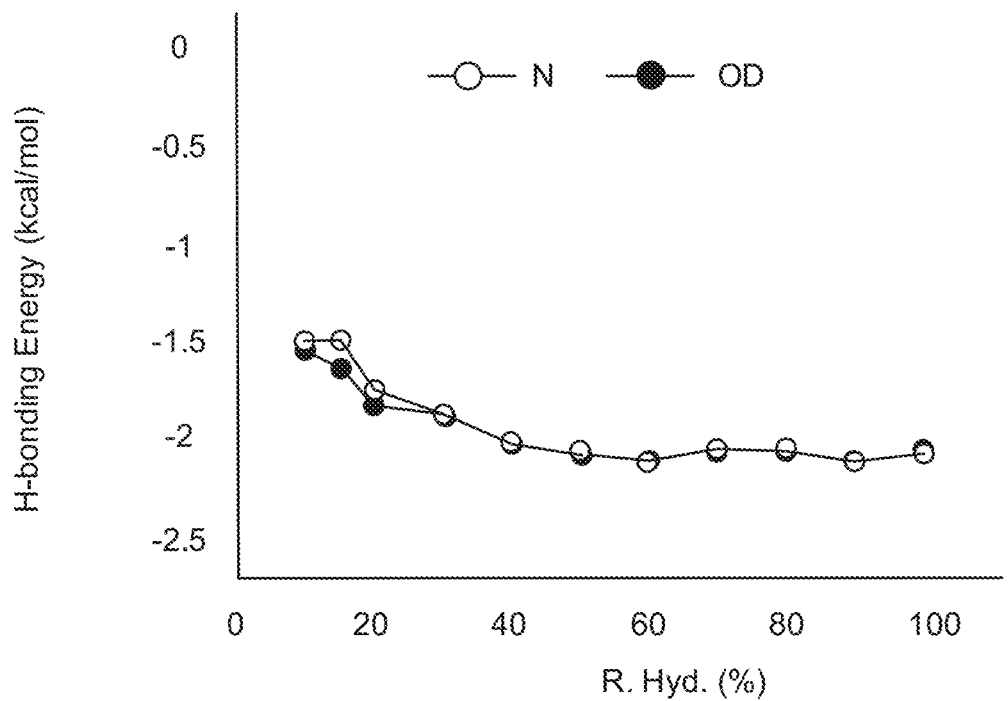
FIG. 4J is a graph depicting energy of side chains vs % RH in DYF.
Figure 4K:
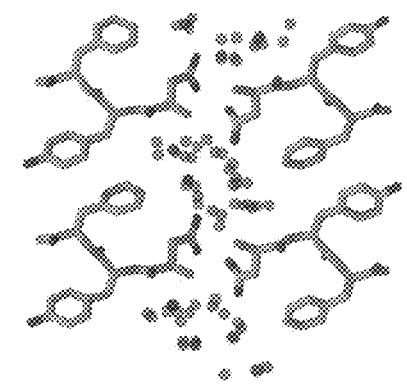
FIG. 4K provide images showing the hydrogen bonding potential of DYF with water and different RH values.
Figure 4K:
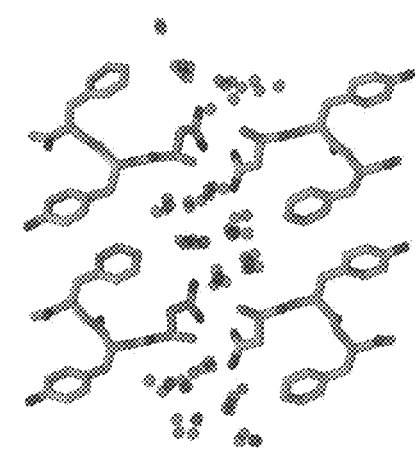
Figure 4K:
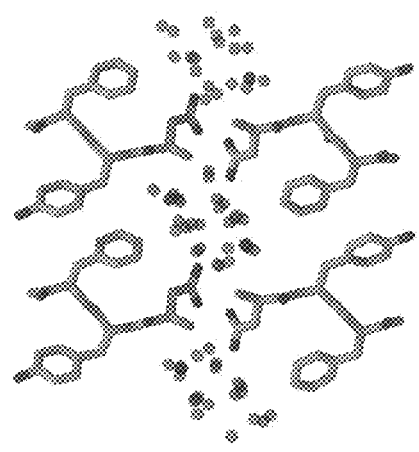
Figure 4L:
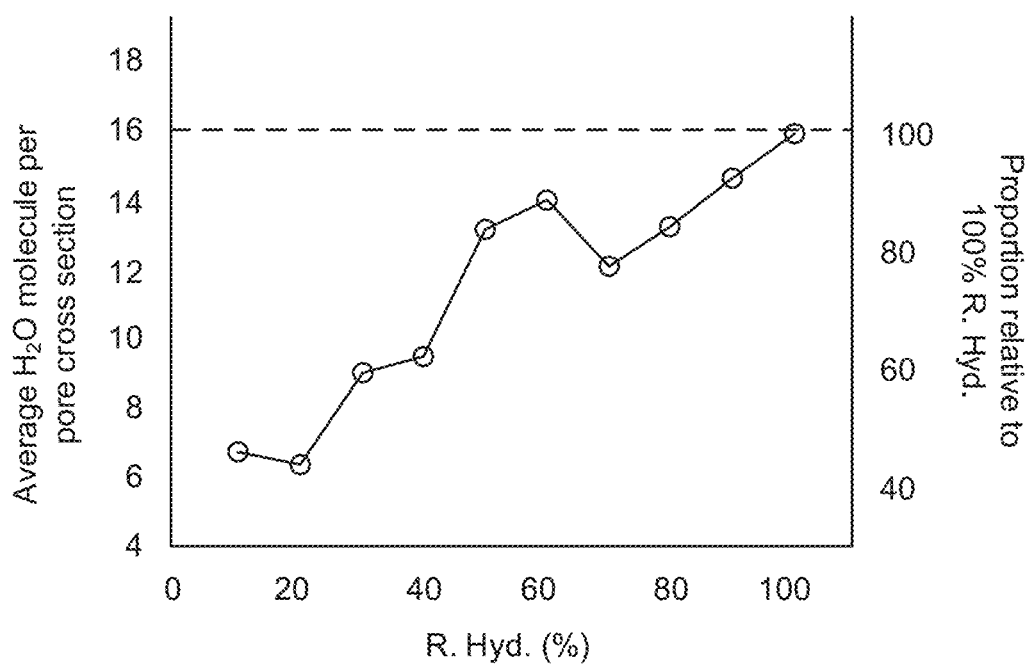
FIG. 4L shows average number of water molecules in the cross-section of the pore over the simulation frames vs. R. Hyd. for DYF.

This understanding is consistent with the lower WR responsive behaviour observed for the DYF crystals, where the pore size is significantly smaller, and the majority of the H-bonding sites exist between the DYF monomers with only the aspartate side chain and the aspartate backbone nitrogen interacting with water molecules (FIG. 4G and FIG. 4H). In contrast to HYF crystals, the occupancy of these H-bonding sites decrease from ~30% at 100% R. Hyd. to ~15% at 10% R. Hyd. (FIG. 4I, FIG. 4J, FIG. 4K). The weaker interactions between the residues at the pore surface and water molecules result in a reduction in the ability to translate energy into structures' elastic energy, which is seen through the consistent reduction in the average number of water molecules in the cross-section of the pore as the humidity decreases (FIG. 4L). These observations suggest that the H-bonding network in the aqueous nanopores between water and the peptide pore surface is crucial to water-responsiveness.

Without wishing to be bound to any particular theory, the crucial role of an integrated H-bonding network at the material/water interface which is connected with deformable regions, observed in HYF crystals, could also be relevant to other naturally occurring and synthetic materials. Clearly, the maximum energy density of a WR material is primarily determined by the total amount of absorbed/desorbed water molecules and their chemical potential during hydration/dehydration cycles. To efficiently convert the chemical potential to mechanical energy, the H-bond network should be strong enough to transfer pressure and volume changes induced by water absorption and desorption to surrounding supramolecular structures—which themselves should be readily deformable—as observed in HYF crystals. The hierarchical organizations can provide high mechanical stiffness and ductility to effectively store energy elastically or transfer it to external loads. These findings provide insights of nature's powerful WR behaviours, and could serve as design criteria for synthetic approaches to develop high energy WR actuators.

Methods:

Abbreviations: HYF (His-Tyr-Phe), DYF (Asp-Tyr-Phe-NH$_2$), YFD (Tyr-Phe-Asp-NH$_2$), PB (phosphate buffer)

Materials and crystal preparation: Tripeptides were purchased from CSBio (purity, >95%) All solvents were bought from Sigma Aldrich. To obtain peptide micro-crystals the YFD, DYF and HYF tripeptides were dissolved to 20 mM in 0.1 M phosphate buffer (PB) at pH 8, vortexed and sonicated. Tripeptides micro-crystals spontaneously formed in the buffered solution within 20 minutes at room temperature. In order to obtain larger crystals for single crystal X-ray diffraction, 5 mM of tripeptide solid was dissolved in 0.1 mM PB, heated to 75° C., left to cool down to room temperature for 72 hrs and kept at 4° C. All the obtained crystals were needle-shaped. For characterization experiments the crystals were washed twice in fresh PB buffer (pH 8).

Tripeptide crystals/polyimide films: The macro scale actuation behaviour of the crystals was demonstrated by gluing the peptide crystals onto polyimide sheets. Briefly, the 8 μm thick polyimide sheet substrate (SPEX) was cut into rectangular pieces of 5 mm length and 3 mm width. The substrates were then cleaned with deionized water and ethanol and allowed to dry for 120 seconds. The polyimide substrates were subsequently placed in a plasma chamber (Fischione M1070 NanoClean) for ionization, thus allowing the surface to hold charge and attract the solution to be deposited more easily. Plasma oxidation was run at 100% power with 75% argon and 25% oxygen gas for 90 seconds. The tripeptide crystals with dimensions ~1.5 μm in width and length ranging from ~30 μm to 110 μm were mixed with Elmer's glue solution (Elmer's Products), and resultant slurry was applied on the substrate using a micropipette (two layers of 13 μL crystal/adhesive mixture). The films costed with crystal/adhesive slurry were then allowed to dry to 40% RH. The curvature of the films was analyzed using Image J software (MG image). Photographs of the curved films were obtained with a digital camera (Canon). The energy density was calculated using Timoshenko's and Stoney's models.

WR actuation speed determination: The humidity cycles were obtained by alternating RH from 10 to 90% by using dry lab air and water-saturated air that passed through a water container for micro (AFM) and macro scale. A humidity sensor was placed in the AFM chamber or humidity box to constantly monitor RH. The crystals were deposited on the polyimide film using the method described above and actuation behavior was recorded using a digital camera. For the micron-scale sample, the topographies of crystals were obtained in 10 and 90% RH in tapping mode (AFM, Multimode 8, Bruker) using SCANASYST-AIR ADM tip for imaging. Upon varying RH, images were collected and analyzed in Nanoscope Analysis 1.9 (Bruker). To eliminate tilt effect of the sample plane, fit command was used followed by the section command to extract topography of the crystal.

Time constants τ were obtained by single-exponential fittings for increasing (wetting) and decreasing (drying) humidity cycles. Each half cycle (either wetting or drying) was approximated by single exponential decay/growth function:

$$y = Ae^{-x/\tau} + y0 \quad (1)$$

$$y = Ae^{x/\tau} + y0 \quad (2)$$

where, A is the amplitude and y0 is the value of y at t=0.

Micron-scale HYF crystals' energy density estimation: The energy density of the micron-scale HYF crystal is estimated by its elastic energy difference between 10% RH and 90% RH:

$$U_m = \tfrac{1}{4}(E_{10} + E_{90})\varepsilon^2 \quad (3)$$

where $E_{10}$ and $E_{90}$ are YM of HYF crystal at 10% RH and 90% RH, respectively. E is the WR strain between 10% RH and 90% RH along the thickness direction.

Single crystal X-ray structure determination: Single crystal data were acquired on a Bruker SMART APEX II diffractometer equipped with a CCD detector. The X-ray beam generated from a sealed Mo tube was monochromated by a graphite crystal and collimated by a MonoCap collimator. The wavelength of the incident beam is 0.71073 Å ($\lambda_{Mo-K\alpha}$). The crystal temperature (100 K) was controlled by an Oxford Cryosystems 700+ Cooler. The HYF, DYF and YFD crystals were mounted on a 0.15 mm MicroMount loop (MiTeGen) for measurement. The 2-dimensional diffraction image data were processed using the APEX2 software (version 2013.12) for data reduction, correction and unit cell refinement. Non-hydrogen atoms were refined with anisotropic displacement parameters, and hydrogen atoms on carbon atoms and N1 and N3 were placed in idealized positions and refined with riding models, and hydrogen atoms on N4, N5, and O3 were found from DF maps and refined with a restrained distance of N—H 0.86 Å and O—H 0.84 Å. All water molecules are disordered and their occupancies were refined.

Powder X-ray diffraction analysis: XRPD data was collected on a Bruker D8 Discover diffractometer fitted with an Anton Paar CHC+ variable temperature chamber and variable humidity generator. The temperature was stable and set for 25° C. The collimated X-rays were generated from a Cu tube (λCu-Kα1.540596 Å). The samples were prepared by grinding single crystals to fine powders in a mortar. The diffraction patterns for crystallized peptides were obtained for two humidity-controlled cycles by 10% step increase/decrease.

Measurements of stiffness and height: Height and stiffness measurements were obtained using a Multimode 8 Atomic Force Microscope fitted with a MESP-V2 cantilever (Bruker). Prior to measurements, the crystals were washed twice in the phosphate buffer. The spring constant of the cantilever was calibrated using thermal tune method, and the average value was 2.5 N/m. Washed crystals were deposited on top of a silicon wafer and left in a dry environment overnight. The humidity was adjusted using dry and humid air and continuously monitored by a sensor that was placed in the AFM chamber. At steady RH, value force vs. deflection curves were obtained. The force vs. displacement curve data was analyzed by Nanoscope analysis software (Bruker). By taking the force difference to ⅔ power and dividing to the distance difference, the slope of linearized Hertz model curve was obtained, which contained the Young's modulus. The force and separation values were inserted into the Hertz model formula:

$$(F)^{2/3} = \left(\frac{4}{3}\frac{E}{(1-\nu)^2}\sqrt{R}\right)^{2/3}\delta \quad (4)$$

where F is the force, R is the tip radius, ν is the Poisson ratio, δ is the indentation depth, and E is the YM. After introducing the tip radius and Poisson ratio of 0.4, YM were calculated.

Fourier-transformed infrared spectroscopy: Peptide crystals were applied between two 2 mm thick $CaF_2$ windows and separated by a 27 μm polytetrafluoroethylene spacer and mounted into a flow cell (Harrick Scientific). The FTIR spectra were acquired in a Bruker Vertex 70 spectrometer with a spectral resolution of 2 cm$^{-1}$. The humidity sensor was placed in close proximity to the sample and a stream of humid air passed through the flow cell to alter humidity.

All spectra were corrected to the phosphate buffer. For peptide crystal analysis constant temperature was assumed throughout the spectra collection to avoid thermal artifacts. For the $H_2O/D_2O$ exchange experiment, HYF crystals were exposed to an environment with saturated $D_2O$ for 24 hours. After the FTIR spectra collection for two hydration and dehydration cycles in $D_2O$, the same sample was re-exposed to $H_2O$, and data were collected during another two cycles.

Dynamic vapor sorption: Water vapor sorption isotherms (sorption/desorption, 2 cycles) were measured on an SMS DVS Advantage 1 (Surface Measurement Systems, Middlesex, UK) at a test temperature of 25° C. Cycles were carried out by 10% step RH increase/decrease. Samples of starting mass ca. 0.3 mg were added to 10 mm diameter quartz pans. Automatic endpoint determination was used for each incremental isotherm step set to 0.002% dm/dt for all steps, with a minimum time per step of 10 min and maximum time per step of 4 h. A nitrogen carrier gas was used at a total gas flow rate of 200 cm$^3$/min the duration of the experiment. Images were captured at the end of each stage to record any visible changes in the samples. DVS Advantage Advanced Analysis Suite version 7.0.13.1 was used to analyse the data to produce a % mass vs actual % RH plot, and an isotherm plot. The sample mass at the end of the test at 5% RH was used as the zero mass for calculations of % mass change.

HYF molecular dynamics simulations: A single channel from the crystal structure was studied in order to investigate the effect of hydration on the dimensions of the crystal. The crystallographic information file (CIF) obtained from the single-crystal X-ray crystallography experiment was opened in CCDC Mercury 3.10.3 and visualised using the crystal packing function. The packed crystal structure was written to a protein data bank (PDB) file, which was then annotated with CHARMM residue and atom names. This channel was comprised of 10 stacked crystals in the Z axis (corresponding to the cell's 'c' vector), including all HYF monomers in direct contact with the water in the pore and those immediately adjacent to these (in order to help maintain the structural integrity of the pore). This channel was surrounded by 15 Angstroms of water at standard density using the solvate plugin for VMD 1.9.3. This structure was taken to be 100% hydration. A protein structure file (PSF) for the CHARMM36 forcefield was generated using the psfgen plugin for VMD. To change the hydration level, water was removed at random such that only n % of the original water remained, where n was the intended hydration level. The hydration levels simulated were 0%, 10%, 15%, 20%, 30%, 40%, 50%, 60%, 70%, 80%, 90% and 100%. Given that this approach is not strictly equivalent to measuring the relative humidity experimentally, the text and figure captions distinguish between the experimental RH and the computational relative hydration (R. Hyd.).

Each of these hydration levels was equilibrated in the NVT ensemble at 300 K for 20 ns (with a 2 fs timestep) using NAMD 2.12 and the CHARMM36 forcefield for proteins.[4] The SETTLE algorithm was used to keep water molecules rigid. Bonds between hydrogen atoms and their bonded heavy atoms were also constrained. The Langevin thermostat was used to maintain the temperature. The central six layers of the crystal were analyzed to see how the inter-layer distance (the average of the backbone C-N distances between layers) and the width of the pore (the average of the histidine CE-tyrosine CE distances, used as a proxy for cell 'a' and 'b' vectors) varied over the course of the simulation. The MDAnalysis package for Python was used to probe these distances.

Hydrogen bond analysis and interpretation: To investigate the hydrogen bonding of the residues closest to the internal surface of the pore, the presence of hydrogen bonds to solvent was investigated for each relative hydration simulation. These bonds were measured using the MDAnalysis library for Python. Hydrogen bonds were defined as a hydrogen bond length of less than 3 Å and a donor-H-acceptor angle of greater than 120° (the default settings). For selected residues, H-bonds were monitored across the 6 central layers for each frame. The average was taken over these six layers across the rotationally symmetric sites in the pore. As simulations were performed in triplicate for each R. Hyd., analysis was performed separately for each trajectory and a mean hydrogen bond formation incidence was obtained for each site, along with a standard deviation. The H-bonding energy is calculated from the occupancy of the site using the Boltzmann factor. That is, this disclosure does not rely specifically on the force field interaction terms to extract the H-bonding energy from the potential energy function. Rather, the Boltzmann distribution was applied to determine the potential energy of the H-bond associated with a given probability for the site to be occupied. The potential energy is estimated by proportional probabilities (Boltzmann factor) averaged from a number of frames in the simulation at each state. A proportionality constant of 1 was assumed. Thus, although the absolute cohesive energy of the water may be proportionally larger or smaller than the reported value the trend and relative magnitudes of the interactions are correct.

What is claimed is:

1. A thin film comprising:
    a flexible polymer layer with a Young's modulus between 100 kPa and 10 GPa; and
    a peptide layer comprising a peptide, wherein the peptide layer is disposed on the flexible polymer layer, the peptide being selected from a group consisting of histidine-tyrosine-phenylalanine (HYF), aspartic acid-tyrosine-phenylalanine (DYF) and tyrosine-phenylalanine-aspartic acid (YFD).

2. The thin film as recited in claim 1, wherein the peptide is histidine-tyrosine-phenylalanine (HYF).

3. The thin film as recited in claim 1, wherein the peptide is aspartic acid-tyrosine-phenylalanine (DYF) with an amidated carboxyl-terminus.

4. The thin film as recited in claim 1, wherein the peptide is tyrosine-phenylalanine-aspartic acid (YFD) with an amidated carboxyl-terminus.

5. The thin film as recited in claim 1, wherein the peptide layer consists of the peptide and an adhesive.

6. The thin film as recited in claim 1, wherein the peptide layer consists of the peptide.

7. The thin film as recited in claim 1, wherein the flexible polymer layer is a polyimide, a polyethylene terephthalate, a polymerized siloxane, a polydimethylsiloxane (PDMS), a silk, a latex rubber, a natural rubber, or a polycarbonate (PCTE).

8. The thin film as recited in claim 1, wherein the thin film consists of the flexible polymer layer and the peptide layer.

9. The thin film as recited in claim 8, wherein the flexible polymer layer has a thickness between 2 µm and 5 mm.

10. The thin film as recited in claim 1, wherein the peptide layer has a thickness between 0.5 µm and 1 mm.

11. The thin film as recited in claim 1, wherein the peptide layer has a Young's moduli between 100 kPa and 10 GPa.

12. The thin film as recited in claim 1, wherein the peptide is a crystal peptide.

* * * * *